Figure 4:
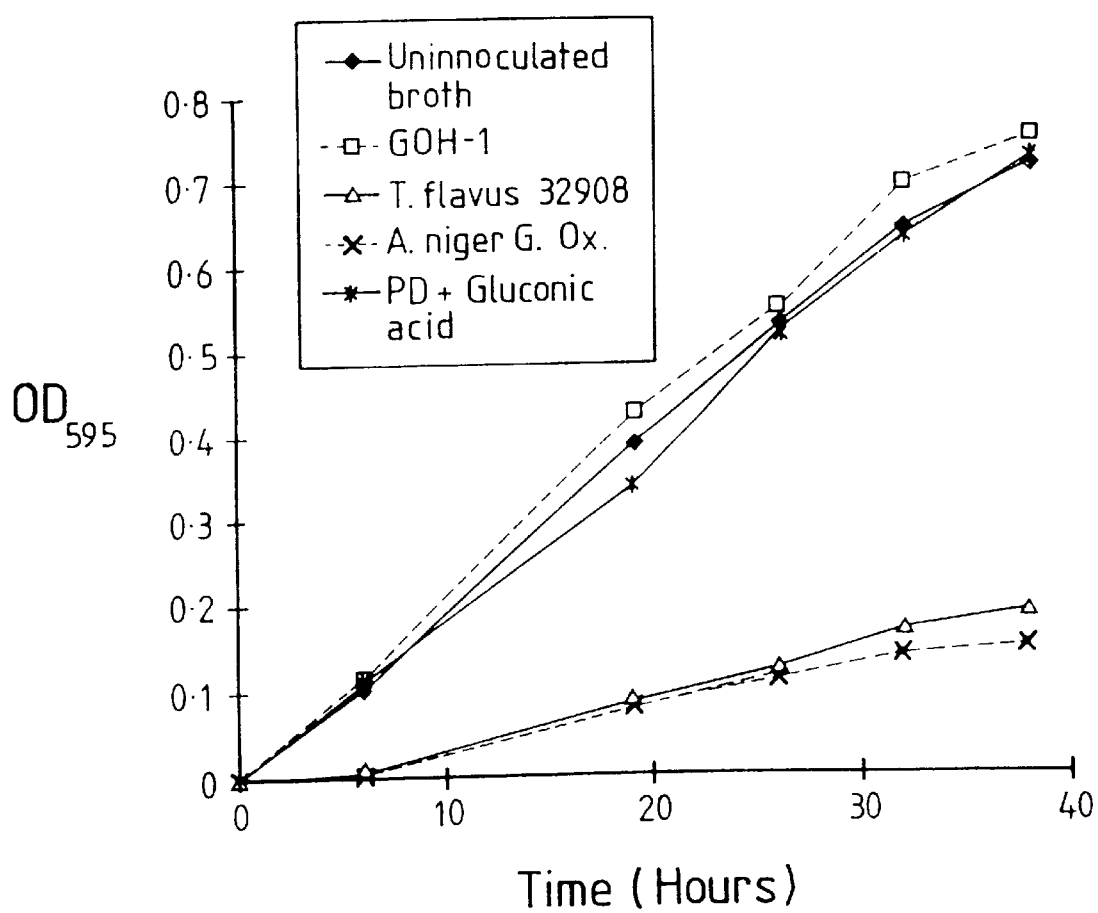

United States Patent [19]
Murray et al.

[11] Patent Number: 6,054,318
[45] Date of Patent: Apr. 25, 2000

[54] EXPRESSION OF THE GLUCOSE OXIDASE GENE IN TRANSGENIC ORGANISMS

[75] Inventors: Fiona Ruth Murray, Macquarie; Danny James Llewellyn, O'Connor; Elizabeth Salisbury Dennis, Yarralumla; William James Peacock, Deakin, all of Australia

[73] Assignee: Commonwealth Scientific And Industrial Research Organization, Campbell, Australia

[21] Appl. No.: 08/693,214

[22] PCT Filed: Feb. 10, 1995

[86] PCT No.: PCT/AU95/00059

§ 371 Date: Nov. 11, 1996

§ 102(e) Date: Nov. 11, 1996

[87] PCT Pub. No.: WO95/21924

PCT Pub. Date: Aug. 17, 1995

[30] Foreign Application Priority Data

Feb. 10, 1994 [AU] Australia ................ PM 3792

[51] Int. Cl.[7] ............... A01H 1/00; C12N 5/14; C07H 21/04; C07K 14/370
[52] U.S. Cl. .............. 435/418; 435/419; 435/320.1; 435/183; 530/370; 530/371; 536/23.2; 536/23.7; 536/24.1; 800/278; 800/279; 800/284; 800/287; 800/288; 800/301
[58] Field of Search .................... 800/278, 279, 800/284, 287, 288, 301; 435/418, 419, 320.1, 183; 536/23.2, 23.7, 24.1; 530/370, 371

[56] References Cited

FOREIGN PATENT DOCUMENTS

| | | |
|---|---|---|
| 40755 | 4/1990 | Australia . |
| 8905344 | 6/1989 | WIPO . |
| WO9002801 | 3/1990 | WIPO . |
| 9007001 | 6/1990 | WIPO . |
| 9214824 | 9/1992 | WIPO . |
| 9215685 | 9/1992 | WIPO . |
| 9315108 | 8/1993 | WIPO . |
| WO9500059 | 2/1995 | WIPO . |
| WO9514784 | 6/1995 | WIPO . |

OTHER PUBLICATIONS

Baetselier et al. J Biotech, 1992, vol. 24, pp. 141–148.
Whittington et al. Curr Genet, 1990, vol. 18, pp. 531–536.
Kim et al., Phytopathology, 78: 488–492, 1988 (Exhibit 1).
Cornelissen et al., Plant Physiology, 101: 709–712, 1993 (Exhibit 2).
Peng et al., Phytopathology, 82: 696–699, 1992 (Exhibit 3).
Chen et al., Science, 262, 1883–1886, 1983 (Exhibit 4).
Hain et a;., Nature, 361: 153–156, Jan. 14, 1993 (Exhibit 5).
Huang et al., Scientia Agricultura Sinica, 3: 32–36, 1986 (Exhibit 9).
Perlak et al., 8: 939–943, Oct. 10, 1990 (Exhibit 11).
Wu et al., The Plant Cell 7:1357–1368 (1995) (Exhibit 2).
Hodgkins, Martin et al., "Expression of the Glucose Oxidase Gene from *Aspergillus niger* in *Hansenula polymorpha* and its use as a Reporter Gene to Isolate Regulatory Mutations," Yeast, 9: 625–635 (1993).
Kim, K. K. et al., "Production, purification and properties of glucose oxidase from the biocontrol fungus *Talaromyces flavus*", Can J. Microbiol, 36: 199–205 (1990); and.
Kim, K. K. et al., "Glucose oxidase as the antifungal principle of talaron from *Talaromyces flavus*", Can J. Microbiol, 36: 760–764 (1990).

*Primary Examiner*—Chris Eisenschenk
*Assistant Examiner*—Phuong T. Bui
*Attorney, Agent, or Firm*—John P. White; Cooper & Dunham LLP

[57] ABSTRACT

A genetic construct for use in production of transgenic plants with reduced susceptibility or increased resistance to pests or diseases comprises an isolated nucleotide sequence encoding the glucose oxidase enzyme of *Talaromyces flavus*, the nucleotide sequence being operably linked to a promoter capable of expression in a plant, plant cell or group of plant cells, and further comprises a nucleic acid segment having a nucleotide sequence encoding a signal sequence which directs secretion of the functional glucose oxidase enzyme of *T. flavus* from plant cells.

21 Claims, 5 Drawing Sheets

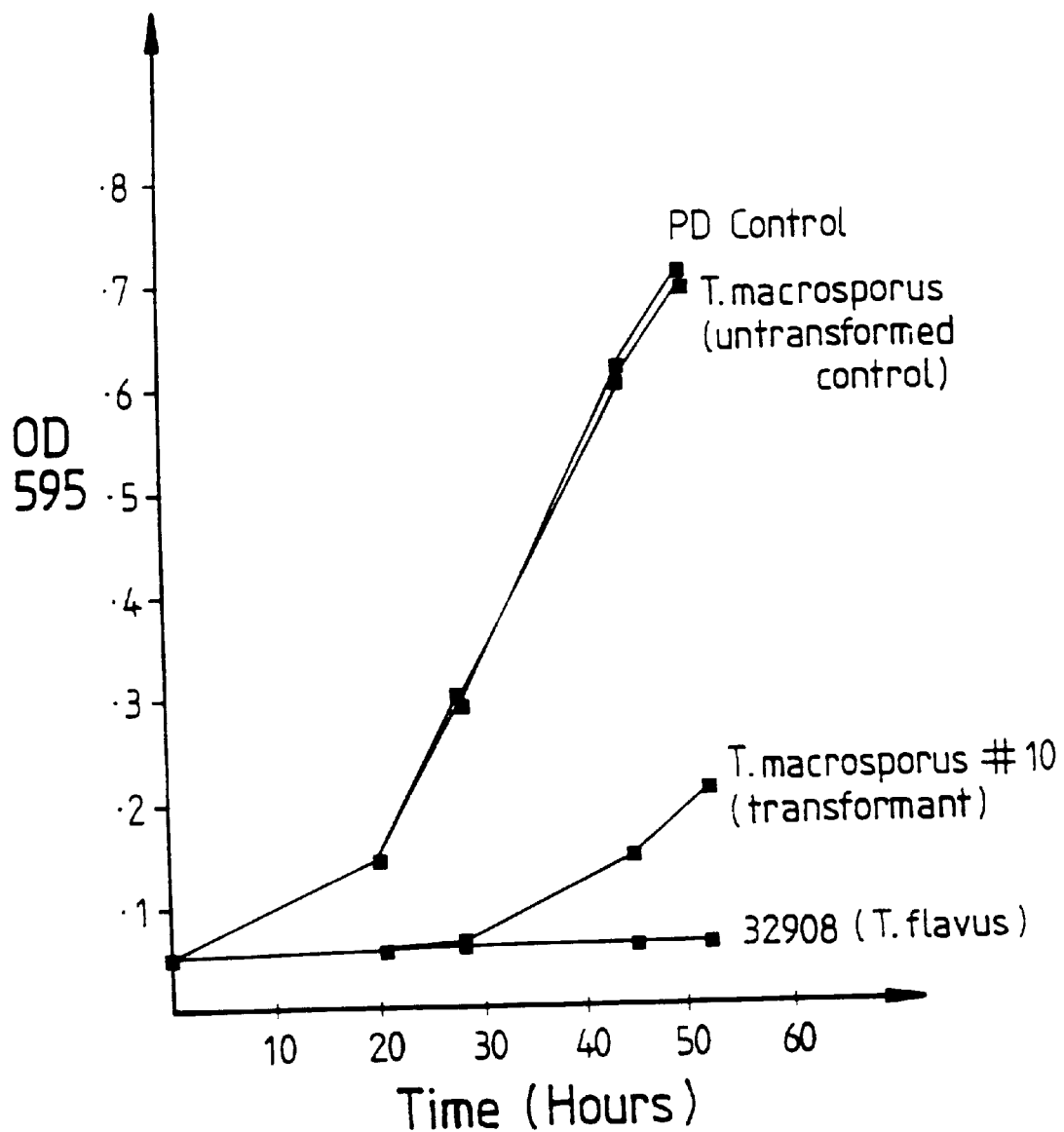

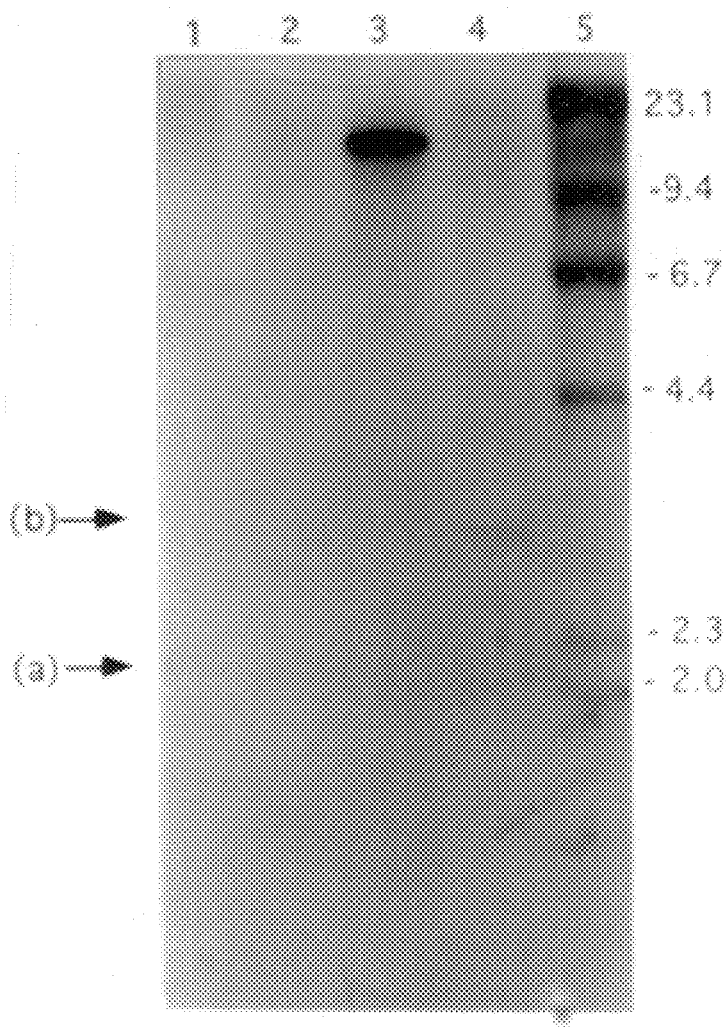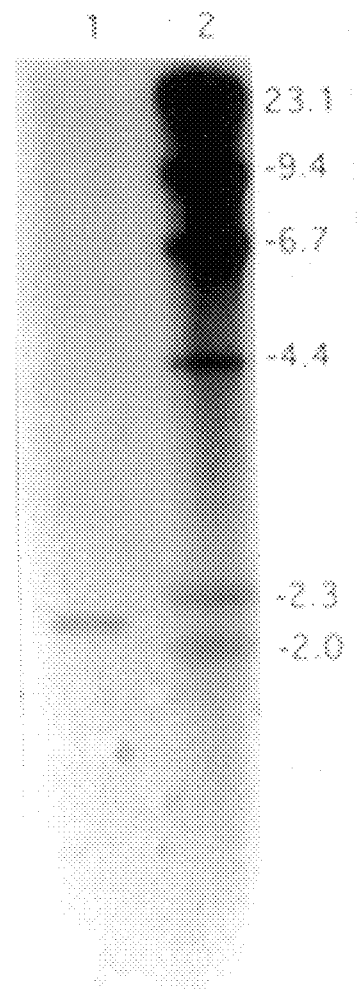

FIG. 3 (A-B)
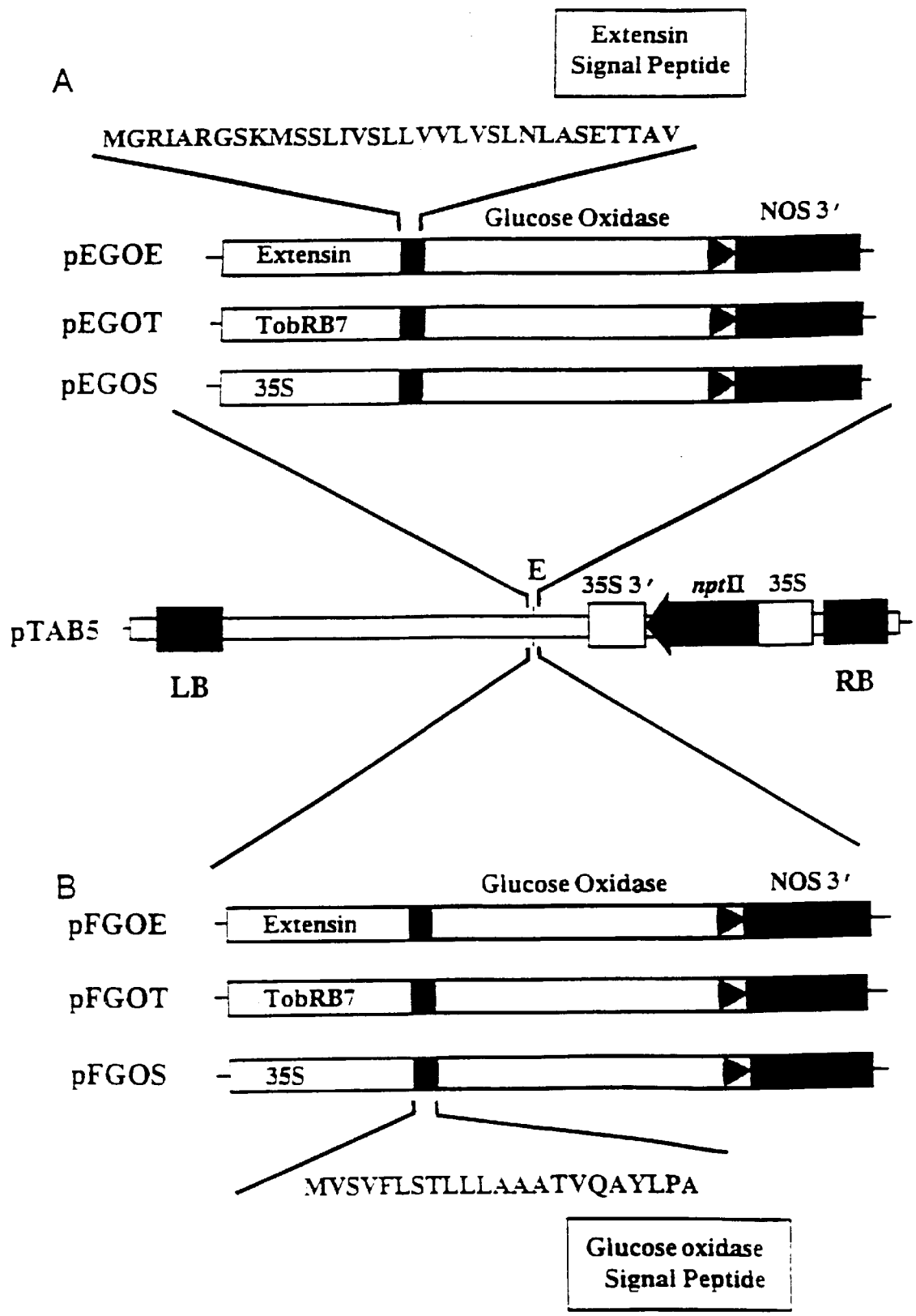

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3029 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Talaromyces flavus
      (B) STRAIN: ATCC 32908

(ix) FEATURE:
      (A) NAME/KEY: CDS
      (B) LOCATION: 1032..2846

(xi) SEQUENCE DESCRIPTION: SEQ ID NO:1:

```
CCACAAGTCC TAGAGAAGAC ACACAGTCTC GAGCCCAAAG TAAGAATGGA TATTGTGACT      60

TCCTAAAGGC CTCACCGGGC AGTGAGGTAT TTGATGTTTA CCAAACGCTA GTATGGGTAG     120

CATAATCGGT GATACCTAGG TATATCATAT GTTCATCCAC AGGGCTGGGT TTGTGAAGAA     180

ACTGTAGCAC TAGTGCTGCT TAGTTGCATA TGGAGTTTCT ATCTGCACTA TTCCGTTGGA     240

GGAAGGAAGA AAAGGGCAAG AGAGATACTG TCAAATGAAT GTACTCGGGG GTCACTGAAT     300

ACGTGAAAGC GTACTTAGGT GATCTATTGC GAGAATAGTT CAATGATATC GATGTCCTCT     360

CGGCGCTCCA CTCTCTCTAT TCGTATCTGA TTCTGATCTG CTCTTCATTC ACAACTTTAT     420

GTATCTGTCA TGCCAGTTTT ACGAGTACTG GGAAAGTTGG CGCTCAGAGC TGGGATTCTT     480

GGGTTTCATT GACGCTCAAC CTAGAGTTTG AATGATATCG CTTTATCTTT AGATAATCTT     540
```

```
CAACGTAACA ATGTGCTTGA GCTTCTAGCG CCAAGATGCG TAGACTTTCG TAAATGGTAG      600

TTCAAGCTAA TAATTCAGGA AAATATTGCA GAGGATTATC GCCACACATG CCGATGGAGC      660

ATACAGACTC CTCTTGATAC GATGCTTTGA CCACTCACAT CCTCCAGCCT TCCATCCAGG      720

TCCCTAGGTT CAGCCGTGCT TCCAGCACTT ACTGATCAAA CCCCTGTAGC ACGGCTAGTA      780

TCTCATATCT TTCCGTCTGC AGCATGAGTC GCTCATGTCT GCACGAGTCC ATTTTCAGAA      840

AGTGGGATAA TCTAACCTGG TGGCGAGGCC AAGATACGAC ATAAAGGAAA TGTTTGCTTC      900

TTGCAAGTCT ATAAATTGAG CGACATCTAC CGCTGTTCAG ACAAGTTCTT CAGCACAACA      960

ATCAGGTAAT TCACCACTC TCCTTGCAAT CCCGTTTATC TTCTCCATCT CCTTGACCTT     1020

GCCGGATCGA A ATG GTG TCT GTA TTT CTC AGC ACT CTT CTT TTA GCC GCG     1070
             Met Val Ser Val Phe Leu Ser Thr Leu Leu Leu Ala Ala
              1               5                  10

GCT ACG GTC CAA GCC TAC CTG CCT GCC CAA CAG ATT GAT GTC CAG TCT      1118
Ala Thr Val Gln Ala Tyr Leu Pro Ala Gln Gln Ile Asp Val Gln Ser
     15              20                  25

AGT CTT CTC AGT GAC CCT AGC AAG GTC GCC GGA AAG ACC TAT GAT TAC      1166
Ser Leu Leu Ser Asp Pro Ser Lys Val Ala Gly Lys Thr Tyr Asp Tyr
 30              35                  40                  45

ATT ATT GCT GGT GGT GGT TTG ACT GGC CTT ACT GTT GCC GCC AAA CTG      1214
Ile Ile Ala Gly Gly Gly Leu Thr Gly Leu Thr Val Ala Ala Lys Leu
                 50                  55                  60

ACA GAA AAC CCC AAG ATC AAA GTC CTG GTT ATT GAA AAG GGC TTC TAT      1262
Thr Glu Asn Pro Lys Ile Lys Val Leu Val Ile Glu Lys Gly Phe Tyr
             65                  70                  75

GAG TCC AAC GAT GGA GCC ATC ATC GAG GAT CCA AAT GCT TAC GGA CAA      1310
Glu Ser Asn Asp Gly Ala Ile Ile Glu Asp Pro Asn Ala Tyr Gly Gln
         80                  85                  90

ATC TTC GGC ACC ACT GTT GAC CAG AAC TAC CTC ACC GTT CCC CTG ATC      1358
Ile Phe Gly Thr Thr Val Asp Gln Asn Tyr Leu Thr Val Pro Leu Ile
     95                  100                 105

AAC AAC CGC ACG AAC AAT ATC AAG GCC GGC AAG GGT CTT GGA GGA TCA      1406
Asn Asn Arg Thr Asn Asn Ile Lys Ala Gly Lys Gly Leu Gly Gly Ser
110                 115                 120                 125

ACC TTG ATA AAC GGT GAC TCT TGG ACT CGC CCG GAC AAA GTC CAG ATT      1454
Thr Leu Ile Asn Gly Asp Ser Trp Thr Arg Pro Asp Lys Val Gln Ile
                 130                 135                 140

GAT TCT TGG GAG AAG GTC TTT GGC ATG GAA GGT TGG AAT TGG GAC AGT      1502
Asp Ser Trp Glu Lys Val Phe Gly Met Glu Gly Trp Asn Trp Asp Ser
             145                 150                 155

ATG TTT GAG TAC ATG AAG AAG GCC GAG GCT GCA CGT GCC CCT ACT GCT      1550
Met Phe Glu Tyr Met Lys Lys Ala Glu Ala Ala Arg Ala Pro Thr Ala
         160                 165                 170

GCT CAA CTT GCT GCC GGT CAC TAC TTC AAT GCT ACC TGC CAT GGA ACT      1598
Ala Gln Leu Ala Ala Gly His Tyr Phe Asn Ala Thr Cys His Gly Thr
     175                 180                 185

AAC GGT ACT GTT CAA TCC GGA GCC CGT GAC AAC GGT CAA CCT TGG TCT      1646
Asn Gly Thr Val Gln Ser Gly Ala Arg Asp Asn Gly Gln Pro Trp Ser
190                 195                 200                 205

CCT ATT ATG AAG GCC CTT ATG AAC ACC GTC TCG GCC CTT GGT GTC CCC      1694
Pro Ile Met Lys Ala Leu Met Asn Thr Val Ser Ala Leu Gly Val Pro
                 210                 215                 220

GTA CAG CAA GAC TTT CTC TGC GGT CAT CCT CGA GGT GTC TCT ATG ATC      1742
Val Gln Gln Asp Phe Leu Cys Gly His Pro Arg Gly Val Ser Met Ile
             225                 230                 235

ATG AAC AAT GTC GAC GAA AAC CAA GTT CGT GTT GAT GCT GCC CGT GCA      1790
Met Asn Asn Val Asp Glu Asn Gln Val Arg Val Asp Ala Ala Arg Ala
```

-continued

```
            240                     245                     250
TGG CTG CTT CCC AGC TAC CAG CGC CCC AAC TTG GAG ATC CTT ACT GGT    1838
Trp Leu Leu Pro Ser Tyr Gln Arg Pro Asn Leu Glu Ile Leu Thr Gly
    255                     260                     265

CAG ATG GTT GGA AAG GTT CTG TTT AAA CAG ACC GCA TCC GGT CCC CAG    1886
Gln Met Val Gly Lys Val Leu Phe Lys Gln Thr Ala Ser Gly Pro Gln
270                     275                     280                     285

GCT GTT GGT GTG AAC TTC GGT ACT AAT AAG GCC GTT AAC TTT GAC GTC    1934
Ala Val Gly Val Asn Phe Gly Thr Asn Lys Ala Val Asn Phe Asp Val
                    290                     295                     300

TTT GCT AAG CAT GAG GTC CTT TTG GCT GCC GGC TCA GCT ATC TCT CCG    1982
Phe Ala Lys His Glu Val Leu Leu Ala Ala Gly Ser Ala Ile Ser Pro
            305                     310                     315

CTG ATC TTG GAA TAT TCT GGC ATA GGC TTG AAG TCT GTT CTT GAT CAG    2030
Leu Ile Leu Glu Tyr Ser Gly Ile Gly Leu Lys Ser Val Leu Asp Gln
        320                     325                     330

GCC AAT GTC ACT CAG CTT CTT GAT CTT CCT GTT GGT ATC AAT ATG CAA    2078
Ala Asn Val Thr Gln Leu Leu Asp Leu Pro Val Gly Ile Asn Met Gln
    335                     340                     345

GAC CAG ACC ACA ACC ACT GTC AGT TCC CGT GCT AGT GCC GCT GGT GCT    2126
Asp Gln Thr Thr Thr Thr Val Ser Ser Arg Ala Ser Ala Ala Gly Ala
350                     355                     360                     365

GGT CAG GGT CAG GCC GTC TTC TTC GCC AAT TTC ACT GAA ACC TTC GGT    2174
Gly Gln Gly Gln Ala Val Phe Phe Ala Asn Phe Thr Glu Thr Phe Gly
                    370                     375                     380

GAC TAC GCC CCC CAG GCC AGA GAG TTA CTC AAC ACC AAG CTT GAC CAA    2222
Asp Tyr Ala Pro Gln Ala Arg Glu Leu Leu Asn Thr Lys Leu Asp Gln
            385                     390                     395

TGG GCT GAG GAG ACC GTT GCG CGA GGT GGT TTC CAT AAT GTA ACT GCT    2270
Trp Ala Glu Glu Thr Val Ala Arg Gly Gly Phe His Asn Val Thr Ala
        400                     405                     410

CTC AAA GTT CAA TAT GAA AAC TAT CGT AAC TGG CTC CTT GAC GAA GAC    2318
Leu Lys Val Gln Tyr Glu Asn Tyr Arg Asn Trp Leu Leu Asp Glu Asp
    415                     420                     425

GTT GCC TTC GCC GAG CTT TTC ATG GAT ACC GAG GGC AAG ATC AAC TTC    2366
Val Ala Phe Ala Glu Leu Phe Met Asp Thr Glu Gly Lys Ile Asn Phe
430                     435                     440                     445

GAC TTA TGG GAT CTC ATC CCT TTC ACT CGT GGT TCC GTC CAT ATC CTC    2414
Asp Leu Trp Asp Leu Ile Pro Phe Thr Arg Gly Ser Val His Ile Leu
                    450                     455                     460

AGT AGC GAC CCT TAC CTA TGG CAA TTC GCC AAC GAC CCC AAA TTC TTC    2462
Ser Ser Asp Pro Tyr Leu Trp Gln Phe Ala Asn Asp Pro Lys Phe Phe
            465                     470                     475

CTG AAC GAG TTT GAC CTC CTT GGT CAA GCC GCT GCT TCC AAG CTT GCT    2510
Leu Asn Glu Phe Asp Leu Leu Gly Gln Ala Ala Ala Ser Lys Leu Ala
        480                     485                     490

CGT GAT CTT ACC AGC CAA GGT GCT ATG AAG GAG TAC TTC GCC GGA GAG    2558
Arg Asp Leu Thr Ser Gln Gly Ala Met Lys Glu Tyr Phe Ala Gly Glu
    495                     500                     505

ACT CTT CCA GGA TAC AAC TTG GTC GAG AAT GCT ACT CTT TCC CAG TGG    2606
Thr Leu Pro Gly Tyr Asn Leu Val Glu Asn Ala Thr Leu Ser Gln Trp
510                     515                     520                     525

TCG GAT TAT GTC TTA CAG AAC TTC CGT CCC AAC TGG CAT GCT GTC AGC    2654
Ser Asp Tyr Val Leu Gln Asn Phe Arg Pro Asn Trp His Ala Val Ser
                    530                     535                     540

AGC TGC TCT ATG ATG TCT AGA GAG CTT GGT GGT GTC GTT GAT GCT ACT    2702
Ser Cys Ser Met Met Ser Arg Glu Leu Gly Gly Val Val Asp Ala Thr
            545                     550                     555

GCC AAG GTG TAC GGT ACG CAG GGC CTA CGT GTC ATT GAT GGC TCT ATT    2750
```

-continued

```
                Ala Lys Val Tyr Gly Thr Gln Gly Leu Arg Val Ile Asp Gly Ser Ile
                    560                 565                 570

CCT CCG ACT CAG GTG TCT TCT CAT GTC ATG ACC ATT TTC TAC GGA ATG                2798
Pro Pro Thr Gln Val Ser Ser His Val Met Thr Ile Phe Tyr Gly Met
575                 580                 585

GCT TTG AAA GTT GCT GAT GCG ATT CTG GAC GAC TAT GCC AAA AGT GCC                2846
Ala Leu Lys Val Ala Asp Ala Ile Leu Asp Asp Tyr Ala Lys Ser Ala
590                 595                 600                 605

TAGAGGTGTC ATGAATCGCG GTTCGTCAGC GAATTTGCTA GGGTTTAGAT CACCGATTTT              2906

TTCTCCTCGC TCATACATTG TTAGATTCTC GCACATATAG ATCGATTTAA ATTGCTTATA              2966

GACAACGTGA AATTTACTAC TTATTCATCG AACTTACATT CTTCAAAATA TTCAAGAGAG              3026

CTC                                                                            3029
```

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
CCTTGCCGAC TAGTAATGGT GT                                                         22
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
CCTACCTGGA TATCCAACAG AT                                                         22
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
TTGGTTGTAC TAGTCATGGG AA                                                         22
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CCACAGCTGT TAACACTTAC TC                                                         22
```

-continued (2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GCGGTCATCC TCGAGGTGTC TCTATG                                              26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TACTCCTTCA TAGCACCTTG GCTGGT                                              26

(2) INFORMATION FOR SEQ ID NO:8:

(i) SEQUENCE CHARACTERISTICS:
        (A) LENGTH: 605 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Ser Val Phe Leu Ser Thr Leu Leu Ala Ala Ala Thr Val
 1               5                  10                  15

Gln Ala Tyr Leu Pro Ala Gln Gln Ile Asp Val Gln Ser Ser Leu Leu
            20                  25                  30

Ser Asp Pro Ser Lys Val Ala Gly Lys Thr Tyr Asp Tyr Ile Ile Ala
        35                  40                  45

Gly Gly Gly Leu Thr Gly Leu Thr Val Ala Ala Lys Leu Thr Glu Asn
    50                  55                  60

Pro Lys Ile Lys Val Leu Val Ile Glu Lys Gly Phe Tyr Glu Ser Asn
65                  70                  75                  80

Asp Gly Ala Ile Ile Glu Asp Pro Asn Ala Tyr Gly Gln Ile Phe Gly
                85                  90                  95

Thr Thr Val Asp Gln Asn Tyr Leu Thr Val Pro Leu Ile Asn Asn Arg
            100                 105                 110

Thr Asn Asn Ile Lys Ala Gly Lys Gly Leu Gly Gly Ser Thr Leu Ile
        115                 120                 125

Asn Gly Asp Ser Trp Thr Arg Pro Asp Lys Val Gln Ile Asp Ser Trp
    130                 135                 140

Glu Lys Val Phe Gly Met Glu Gly Trp Asn Trp Asp Ser Met Phe Glu
145                 150                 155                 160

Tyr Met Lys Lys Ala Glu Ala Ala Arg Ala Pro Thr Ala Ala Gln Leu
                165                 170                 175

Ala Ala Gly His Tyr Phe Asn Ala Thr Cys His Gly Thr Asn Gly Thr
            180                 185                 190

Val Gln Ser Gly Ala Arg Asp Asn Gly Gln Pro Trp Ser Pro Ile Met
```

-continued

```
                195                 200                 205
Lys Ala Leu Met Asn Thr Val Ser Ala Leu Gly Val Pro Val Gln Gln
        210                 215                 220
Asp Phe Leu Cys Gly His Pro Arg Gly Val Ser Met Ile Met Asn Asn
225                 230                 235                 240
Val Asp Glu Asn Gln Val Arg Val Asp Ala Ala Arg Ala Trp Leu Leu
                245                 250                 255
Pro Ser Tyr Gln Arg Pro Asn Leu Glu Ile Leu Thr Gly Gln Met Val
                260                 265                 270
Gly Lys Val Leu Phe Lys Gln Thr Ala Ser Gly Pro Gln Ala Val Gly
            275                 280                 285
Val Asn Phe Gly Thr Asn Lys Ala Val Asn Phe Asp Val Phe Ala Lys
        290                 295                 300
His Glu Val Leu Leu Ala Ala Gly Ser Ala Ile Ser Pro Leu Ile Leu
305                 310                 315                 320
Glu Tyr Ser Gly Ile Gly Leu Lys Ser Val Leu Asp Gln Ala Asn Val
                325                 330                 335
Thr Gln Leu Leu Asp Leu Pro Val Gly Ile Asn Met Gln Asp Gln Thr
                340                 345                 350
Thr Thr Thr Val Ser Ser Arg Ala Ser Ala Ala Gly Ala Gly Gln Gly
            355                 360                 365
Gln Ala Val Phe Phe Ala Asn Phe Thr Glu Thr Phe Gly Asp Tyr Ala
        370                 375                 380
Pro Gln Ala Arg Glu Leu Leu Asn Thr Lys Leu Asp Gln Trp Ala Glu
385                 390                 395                 400
Glu Thr Val Ala Arg Gly Gly Phe His Asn Val Thr Ala Leu Lys Val
                405                 410                 415
Gln Tyr Glu Asn Tyr Arg Asn Trp Leu Leu Asp Glu Asp Val Ala Phe
                420                 425                 430
Ala Glu Leu Phe Met Asp Thr Glu Gly Lys Ile Asn Phe Asp Leu Trp
            435                 440                 445
Asp Leu Ile Pro Phe Thr Arg Gly Ser Val His Ile Leu Ser Ser Asp
        450                 455                 460
Pro Tyr Leu Trp Gln Phe Ala Asn Asp Pro Lys Phe Phe Leu Asn Glu
465                 470                 475                 480
Phe Asp Leu Leu Gly Gln Ala Ala Ser Lys Leu Ala Arg Asp Leu
                485                 490                 495
Thr Ser Gln Gly Ala Met Lys Glu Tyr Phe Ala Gly Glu Thr Leu Pro
                500                 505                 510
Gly Tyr Asn Leu Val Glu Asn Ala Thr Leu Ser Gln Trp Ser Asp Tyr
            515                 520                 525
Val Leu Gln Asn Phe Arg Pro Asn Trp His Ala Val Ser Ser Cys Ser
        530                 535                 540
Met Met Ser Arg Glu Leu Gly Gly Val Val Asp Ala Thr Ala Lys Val
545                 550                 555                 560
Tyr Gly Thr Gln Gly Leu Arg Val Ile Asp Gly Ser Ile Pro Pro Thr
                565                 570                 575
Gln Val Ser Ser His Val Met Thr Ile Phe Tyr Gly Met Ala Leu Lys
                580                 585                 590
Val Ala Asp Ala Ile Leu Asp Asp Tyr Ala Lys Ser Ala
            595                 600                 605
```

EXPRESSION OF THE GLUCOSE OXIDASE GENE IN TRANSGENIC ORGANISMS

FIELD OF THE INVENTION.

This invention relates to the production of the transgenic organisms (including for example, plants, microbes and viruses) that express a glucose oxidase gene whose gene product is toxic to economically important pests and diseases of crops. Transgenic plants in accordance with this invention can be sold as improved varieties, whilst transgenic microbes and viruses can be used as biopesticides or as seed coatings or inoculums for soil incorporation.

BACKGROUND OF THE INVENTION.

Production of most crop species is limited by the ravages of pests and diseases. Considerable expense is involved in the protection of crops from these organisms and many current conventional breeding programs are directed at increasing host plant resistance to a variety of invertebrate pests and fungal or viral diseases. Traditional sources of host plant resistance are limited to the same species or species closely related to the crop, but with the advent of genetic engineering novel sources of resistance outside the crop genera are being accessed. Two classic examples are the insecticidal protein genes from *Bacillus thuringiensis* active against a multitude of insect species (Perlak et al., 1990) and the viral coat protein genes that confer tolerance to a variety of related viral diseases (Powell et al., 1986). Transgenic plants expressing these genes have enormous potential markets once the regulatory hurdles are overcome for their large scale release into agriculture.

New sources of host plant resistance are being sought from a variety of sources, and work leading to the present invention has led to the isolation and characterisation of a glucose oxidase gene from the fungus *Talaromyces flavus* that has potential for the control of both fungal diseases and arthropod pests when expressed in transgenic crop plants. The particular examples investigated to date are for the control of the cotton pathogen, *Verticillium dahliae*, the causal agent of verticillium wilt disease, and for the control of Helicoverpa spp. which are economically important Lepidopteran pests of cotton and most summer crops. Use of the glucose oxidase gene for the control of other fungal diseases or pests such as nematodes, mites, aphids, whiteflies, jassids or mirids which are susceptible to hydrogen peroxide produced by glucose oxidase activity is also possible.

Verticillium Wilt as a Cotton Pathogen

Verticillium wilt is a wide-spread disease which affects many different plant species. It is caused by the soil fungus *Verticillium dahliae* (Leb.), an imperfect fungus first isolated from diseased dahlias in 1913 (Muller, 1928). Isolates of the species vary widely in both morphology and pathogenicity but all produce small, hard black structures called microsclerotia. These structures are composed of melanized cells which store many nutrients and are the means by which *V. dahliae* survives in the soil.

*V. dahliae* does not grow saprophytically through the soil, but conidia and microsclerotia germinate in soil if root exudate from desirable plant species are present. The mycelium then invades the plant, entering through the cap of the root region of elongation, root hairs or lower hypercotyl region. In all cases both intercellular and intracellular invasion occurs. In "susceptible" hosts, the fungus successfully penetrates the vascular system of the plant. Here hyphal multiplication occurs and conidiospores are generated which then travel upwards through the xylem thus spreading the fungus rapidly through the vascular system of the plant.

Once spread throughout the vascular system the main effect of the pathogen is to disrupt the passage of water through the stem. This may be attributed to the physical presence of the mycelium of the pathogen, the development of tyloses that block the xylem or to gummosis within the vessels. Further xylem occlusion is caused by high molecular weight polysaccharides produced by the pathogen or cleaved from the plant walls by hydrolytic enzymes. Together this can result in a 40 to 60-fold increase in the resistance of the stem to water flow; thus the characteristic wilting of leaves occurs (Ayer and Racok, 1990).

In cotton more obvious symptoms include a yellowing of lower leaves, vascular discolouration and stunting of plant growth. Some *V. dahliae* isolates also cause severe defoliation of the cotton plant. On the basis of heterokaryon incompatibility tests these isolates fall into a separate group from the less severe, non-defoliating isolates (Puhalla, 1979). All Australian isolates so far examined belong to the less severe, non-defoliating group, however they are still capable of causing a significant reduction in lint yield.

Controlling verticillium wilt in cotton in Australia has frequently been a problem, particularly in the cooler growing regions (New South Wales and Southern Queensland) where cooler, wetter seasons promote more vigorous fungal growth. The microsclerotia produced are resistant to many soil fumigants and remain viable in the soil for many years. Crop rotation is also not a satisfactory control measure because of the wide host range of the fungus. No natural resistance to Verticillium has been identified in cotton, any natural tolerance that has been found is being exploited by the breeders.

Biological control of the pathogen with other microbes is a possible solution. Marios et al. (1982) investigated the potential of over 30 different soil fungi to control verticillium wilt development in eggplant under field conditions. An isolate of *Talaromyces flavus* was identified that reduced disease symptoms by approximately 70% in two separate field situations. Trials have shown that *T. flavus* is able to occupy the rhizosphere of Australian cotton. Further trials will need to be done to determine if this naturally occurring strain or improved engineered strains can control verticillium wilt. However, even if successful, *T. flavus* itself may not be a suitable control agent as large scale seeding of soil in which cotton is to be grown may be impractical and other microbes that live in close association with the cotton plant may be more effective delivery systems.

Helicoverpa spp. are serious pests of cotton and other summer crops.

*Helicoverpa armigera* and *H. puctigera* are two of the most economically important insect pests in many cropping systems in Australia (Fitt, 1989). Their larvae cause considerable damage in crops such as cotton and their control requires the application of vast amounts of chemical pesticides. Many of these pesticides are becoming ineffective due to the development of resistance by the insects and sources of host plant resistance in the crop would be extremely valuable, both economically and environmentally.

Adult moths lay their eggs singly, generally on the young growing tips of the plant. When the neonates emerge they feed on the egg case and then migrate to the young flower buds (squares) and begin to graze. A single larvae may visit several flower buds rather than staying on one square for extended periods of time. Relatively small amounts of feeding damage cause flower abortion and hence the economic threshold for larvae on plants is relatively low. As little as one larvae per meter of cotton row can have a significant effect on yield, so relatively low infestations must be sprayed to control the insect. As indicated below, glucose oxidase is toxic to these caterpillars when incorporated into synthetic diets containing a source of glucose and so may be a useful gene to express in young cotton tissues such as leaves and squares.

Talaromyces flavus is a glucose oxidase secreting ascomycete.

*Talaromyces flavus* (Klocker) Stolk and Samson (anamorph *Penicillium dangeardii* Pitt, usually reported as *P. vermiculatum* Dangeard) is the most common species of its genus. This ascomycete is frequently isolated from soil, although it may also occur in other organic substrates. It is widely distributed around the world but is more commonly found in warmer regions. It has been reported as a potential biocontrol agent for several other fungal pathogens, *Rhizoctonia solani* (Boosalis, 1956) and *Sclerotinia sclerotiorum* (McLaren et al., 1986).

In the above cases, *T. flavus* controls the pathogens by mycoparasitism, that is *T. flavus* parasitises its fungal host for nutrient gain. Infection studies of *S. sclerotiorum* and *R. solani* have shown *T. flavus* coils around the host developing hyphal branches which then penetrate the host's cells. Deterioration of the cytoplasm follows with the infected cells eventually collapsing, although the cell walls remain intact. Transmission electron micrographs of *V. dahliae* microsclerotia parasitised by *T. flavus* have similarly shown cell invasion and lysis taking place only at the contact sites between the host's cells and *T. flavus* hyphal tips (Madi et al., 1989).

The mechanisms involved in the parasitic interactions are unclear. However Fravel et al., (1987) found *T. flavus* secreted a metabolite into liquid medium which in the presence of glucose was toxic to microsclerotia and inhibited radial growth of Verticillium mycelia. The active component was subsequently identified as glucose oxidase secreted from fungal hyphae (Kim et al., 1988). This enzyme has now been shown to inhibit other fungi including several of the Pythium species, *Rhyzoctonia solani* and *Sclerotinia minor* (Kim et al., 1990[a,b]).

Glucose oxidase leads to the production of hydrogen peroxide, ($H_2O_2$) as a by-product of glucose oxidation:

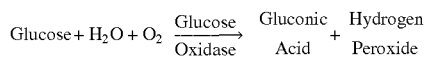

$$\text{Glucose} + H_2O + O_2 \xrightarrow{\text{Glucose Oxidase}} \text{Gluconic Acid} + \text{Hydrogen Peroxide}$$

When added to growth media, hydrogen peroxide inhibited microsclerotial germination and mycelial growth. The other reaction components, glucose oxidase (no glucose present), gluconic acid and glucose did not cause inhibition (Kim et al., 1988). Thus the antifungal activity of glucose oxidase is due to the hydrogen peroxide it produces. However when the peroxide scavenger catalase was added to the culture filtrate of *T. flavus* there was only a loss of 50% of its toxic activity towards *V. dahliae* (Madi et al., 1989). Thus *T. flavus* may produce other agents toxic to *V. dahliae*. *T. flavus* has been found to excrete a range of lytic enzymes including cellulases, β-1-3-glucanases and chitinase. Therefore the antagonistic activity of *T. flavus* towards *V. dahliae* may be due to a combined effect of lytic enzymes and toxic metabolites. The glucose oxidase may act by inhibiting the Verticillium and thus predispose the hyphae to infection before contact occurs.

Glucose oxidase the active agent in the antagonism by *T. flavus* of *V. dahliae*.

The enzyme glucose oxidase is known to be produced by different species of Aspergillus and Penicillium, by *Talaromyces flavus* and by the basidiomycete *Phanerochaete chryosporium*, (white rot fungus). In *P. chryosporium* (found in wood), the hydrogen peroxide produced is required by a ligninase enzyme for the degradation of lignin. In the other fungi little is known about the enzyme's biological function. They may produce enzymes which utilise hydrogen peroxide as *P. chryosporium* does. In this case the enzyme's ability to inhibit various other soil fungi may be a secondary effect, however it would benefit the host in certain competition situations.

Glucose oxidase has been purified from each of the four fungal genera known to produce it. In all cases, the enzyme is a dimeric flavoprotein with an optimum pH of 5.0. The most distinct enzyme is that of *P. chryosporium*. Unlike the others it is not glycosylated and although glucose is its primary substrate it is also induced to a smaller degree by sorbose, xylose and maltose (33, 13 and 7% respectively) (Kelly and Reddy, 1986). The other enzymes are highly specific for β-D-Glucose.

Glucose oxidase from *T. flavus* has a relative molecular weight of 164,000 (subunit molecular weight 71,000) (Kim et al., 1990). This is similar to that of *Penicillium amakienase* (150,000) and *Aspergillus niger* (152,000), (Nakamura and Fujiki, 1968). It is stable from pH 3.0 to 7.0, unlike *A. niger* which is restricted to pH 4.5 to 6.5. Six isozymes with pI values of 4.40 to 4.55 have been detected. These are thought to be due to differences in sugar residues as opposed to differences in amino acid sequence. It has a relatively low affinity for glucose with a Km for β-D-glucose of 10.9 mM. This is however a higher affinity than that of *A. niger* which has a Km for β-D-glucose of 27 mM.

The gene for glucose oxidase from *A. niger* has been cloned by several groups (Kriechbaum et al., 1989, Frederick et al., 1990, Whittington et al., 1990). The structural gene consists of 1815 bp encoding 605 amino acid residues. The mature protein contains 583 amino acids, the difference being due to 22 amino acids which comprise the secretion signal presequence. No introns were present in the coding region. The gene has been introduced into *Aspergillus nidulans* and the yeast *Saccharomyces cerevisiae* where it provided the novel capacity to produce glucose oxidase. It has also been reintroduced into *A. niger* where increased copy number increased glucose oxidase production.

In the past, biological control of pests and diseases has focussed on natural biocontrol agents such as antagonistic bacteria and fungi or viruses. It has now been found that the effectiveness of these agents can be enhanced if they are engineered to express the glucose oxidase activity. The present invention therefore includes the use of other vectors for delivering the glucose oxidase activity to the pest or pathogen, such as root or leaf colonising micro-organisms which could be beneficial bacteria or fungi that live around the plant and that could exert their effects on plant pests in the rhizosphere or phylloplane or, for example, insect specific viruses that could be sprayed onto the plants.

SUMMARY OF THE INVENTION.

The present invention provides a genetic construct comprising an isolated nucleotide sequence encoding, or complementary to a sequence encoding, the enzyme glucose oxidase or a functional derivative of the enzyme, said nucleotide sequence being operably linked to a promoter capable of expression in a host organism.

By the term "isolated nucleotide sequence" is meant a genetic sequence in a non-naturally-occurring condition. Generally, this means isolated away from its natural state or synthesized or derived in a non-naturally-occurring environment. More specifically, it includes nucleic acid molecules formed or maintained in vitro, including genomic DNA fragments, recombinant or synthetic molecules and nucleic acids in combination with heterologous nucleic acids.

Any suitable promoter may be incorporated in the genetic construct of the present invention. By way of example only, the promoter may be the promoter of the 35S transcript of cauliflower mosaic virus or the tobacco root-specific promoter pTOBRB7.

The terms "genetic sequence" and "nucleotide sequence" are used herein in their most general sense and encompass any contiguous series of nucleotide bases specifying directly, or via a complementary series of bases, a sequence of amino acids in the enzyme glucose oxidase. Such a sequence of amino acids may constitute a full-length glucose oxidase, or an active truncated form thereof, or may correspond to a particular region such as an N-terminal, C-terminal or internal portion of the enzyme.

The genetic construct of the present invention may be introduced into a host organism such as a plant, bacterium or virus in order to provide the host organism with glucose oxidase activity, or elevate endogenous glucose oxidase activity, in the host organism. Reference herein to the elevation of glucose oxidase activity relates to an elevation in activity of up to 30% or more preferably of 30–50%, or even more preferably 50–75% or still more preferably 75% or greater above the normal endogenous or existing levels of glucose oxidase activity of the host organism.

The nucleic acids of the genetic constructs of the present invention may be ribonucleic acid or deoxyribonucleic acids, single or double stranded and linear or covalently closed circular molecules. Preferably, the nucleotide sequence is cDNA. The present invention also extends to other nucleotide sequences which hybridize under low, preferably under medium and most preferably under high stringency conditions with the nucleotide sequence of the present invention and in particular to the sequence of nucleotides set forth in SEQ ID. NO:1 hereinafter or a part or region thereof. In its most preferred embodiment, the present invention extends to a genetic construct, having a nucleotide sequence set forth in SEQ ID. NO:1 or to a construct having at least 40%, more preferably at least 45%, even more preferably at least 55%, still more preferably at least 65–70%, and yet even more preferably greater than 85% similarity at the level of nucleotide or amino acid sequence to at least one or more regions of the sequence set forth in SEQ ID. NO: 1 and wherein the construct encodes or is complementary to a sequence which encodes an amino acid sequence having glucose oxidase activity.

In this regard, the nucleic acid may include the naturally-occurring nucleotide sequence encoding glucose oxidase or it may contain single or multiple nucleotide substitutions, deletions and/or additions to said naturally-occurring sequence. The nucleic acid of the present invention or its complementary form may also encode a non-full length portion of this enzyme which retains the glucose oxidase activity.

The nucleotide sequence or its complementary form may encode the full-length glucose oxidase enzyme, or a functional derivative thereof. By "functional derivative" is meant any single or multiple amino acid substitution, deletion and/or addition relative to the naturally-occurring enzyme and which retains glucose oxidase activity.

Amino acid insertional derivatives of the glucose oxidase enzyme include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 1 hereunder.

Where the glucose oxidase is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989).

TABLE 1

Suitable residues for amino acid substitutions.

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Other examples of recombinant or synthetic mutants and derivatives of the glucose oxidase enzyme of the present invention include single or multiple substitutions, deletions and/or additions of any molecule associated with the enzyme such as carbohydrates, lipids and/or proteins or polypeptides.

The term "functional derivatives" also extends to any functional chemical equivalent of the glucose oxidase and also to any amino acid derivative described above. For convenience, reference to "glucose oxidase" herein includes reference to any mutants, derivatives, analogues, homologues or fragments thereof.

The present invention is exemplified using an isolated nucleotide sequence derived from *Talaromyces flavus* as set forth in Table 2 (SEQ. ID No:1) since this represents the most convenient and preferred source of material to date. However, one skilled in the art will immediately appreciate that similar sequences can be isolated from any number of sources. All such nucleic acid sequences encoding directly or indirectly a glucose oxidase enzyme, regardless of their source, are encompassed by the present invention.

The genetic construct contemplated herein may exist in combination with a vector molecule, for example an expression-vector. The term "vector molecule" is used in its broadest sense to include any intermediate vehicle for the nucleic acid molecule, capable of facilitating transfer of the nucleic acid into a host organism and/or facilitating integration into the host genome. Where the host organism is a plant, the intermediate vehicle may, for example, be adapted for use in electroporation, microprojectile bombardment, Agrobacterium-mediated transfer or insertion via DNA or RNA viruses. The intermediate vehicle and/or the nucleic acid molecule contained therein may or may not need to be stably integrated into the plant genome. Such vector molecules may also replicate and/or express in prokaryotic cells. Preferably, the vector molecules or parts thereof are capable of integration into the host genome. The genetic construct may additionally contain a promoter sequence operably linked to, and capable of directing expression of, the nucleic acid molecule in the host organism. The nucleic acid molecule and promoter may also be introduced into the host organism by any number of means, such as those described above.

In another aspect, the present invention also provides a transgenic organism capable of expressing a cloned nucleotide sequence encoding the enzyme glucose oxidase or a functional derivative thereof. As described above, the transgenic organism is preferably a plant, for example a cotton plant, or a micro-organism or virus, particularly a root- or leaf-colonising micro-organism or an insect-specific virus.

In a preferred embodiment the cloned nucleotide sequence is the *Talaromyces flavus* glucose oxidase gene as represented by the nucleotide sequence of SEQ ID. No:1, however it will be understood that glucose oxidase genes from other organisms are also encompassed within the scope of the invention.

The invention therefore comprises the expression of the cloned *T. flavus* glucose oxidase gene or other sources of glucose oxidase genes in a transgenic organism, which may be either a plant or a virus or microbe that is brought into contact with a pest species, insect, other arthropod, nematode or disease causing microbe for the control of that pest or disease organism.

The invention may also include the expression of a second gene for the generation of the glucose required for the toxic effect exerted by the glucose oxidase enzyme.

In work leading to the present invention, the antifungal activity of *T. flavus* glucose oxidase in vitro has been demonstrated, as has the insecticidal activity of glucose oxidase in synthetic diets. The glucose oxidase gene from *T. flavus* has been cloned and sequenced, and the functionality of the cloned gene has been established by expression of the cloned glucose oxidase gene in a transgenic fungus originally lacking glucose oxidase activity, and by demonstration of in vitro fungal antagonism by this strain.

In addition, a number of genetic constructs have been made to express the *T. flavus* glucose oxidase gene using standard cloning methods, and these constructs have been transformed into plants using known transformation vectors and protocols to obtain the expression of functional glucose oxidase in the transgenic plants. Transgenic plants expressing glucose oxidase were found to be more tolerant to fungal infection than control plants.

Glucose oxidase can be expressed in transgenic plants.

The expression of the fungal glucose oxidase in transgenic plants poses a number of problems, not the least of which is that the enzyme may have some toxic side effects on the plant itself. The enzyme is excreted from the fungal cell and needs to be equipped with appropriate signals for secretion by plant cells. A number of gene constructs have been constructed to express the *T. flavus* gene both constitutively, tissue specifically and conditionally in transgenic plants. In initial experiments, tobacco (*Nicotiana tabacum*) was used as a recipient because of the long time frame for the generation of transgenic cotton. The different gene constructs were assembled by standard cloning methods (Sambrook et al., 1989), fused to a 3' end from nopaline synthase (NOS 3') and transformed into plants using the binary transformation vectors and protocols of An et al. (1985). The salient features are the type of promoter and the signal sequence at the N-terminal end of the translated glucose oxidase protein. Cellular targeting may be important for the effective expression of the fungal glucose oxidase in other species. It appears that the fungal signal peptide necessary for the excretion of the glucose oxidase protein in Talaromyces is not functional in plants as the native coding region was not expressed in transgenic tobacco tissues. The form of the signal peptide has many options but in one preferred form has the signal sequence from the carrot root extensin gene (Chen & Varner, 1985) and when introduced into transgenic tobacco this modified coding region did produce a functional glucose oxidase protein. The promoter may be any plant promoter resulting in high levels of expression of the introduced glucose oxidase gene. The promoters of the 35S transcript of cauliflower mosaic virus (Odell et al., 1985) or the tobacco root-specific promoter pTOBRB7 (Conkling et al., 1990) have been used, and both produced detectable levels of expression of the glucose oxidase gene in transgenic tobacco when assayed with the coupled peroxidase assay of Fiedurek et al., (1986).

Further features of the present invention will be apparent from the accompanying drawings.

In the drawings:

FIG. 1 shows growth inhibition of Verticillium by culture filtrates from *T. flavus*. Verticillium growth was monitored by light scattering at 595 nm using an automated micro-titre plate scanner. Each well continued 200 μl of Potato Dextrose medium supplemented with culture filtrates from *T.flavus* 32908, *T.flavus* (var macrosporus) a non-glucose oxidase producer, a glucose oxidase positive transformant of var macrosporus or PD medium as a control. Each experiment contained approximately the same amount of glucose oxidase activity (approx. 1.5μg).

FIGS. 2A and 2B show hybridisation of *A. niger* glucose oxidase gene to genomic DNA digests at different stringencies. FIG. 2A: Autoradiograph of a Southern blot of BamH 1 digests of DNA hybridised with $^{32}$P labelled *A. niger* glucose oxidase gene. Hybridisation performed at 37° C. and filter washed with 1×SSC at room temperature. Lane 1, *T. flavus* 26015 DNA; lane 2, *T. flavus* 32908 DNA; lane 3, *A. niger* 9029 DNA; lane 4, *A. nidulans* DNA; lane 5, Hind III digest of $^{32}$P-labelled 1 DNA. Faint bands in lanes 1 and 2 are arrowed. FIG. 2B: Autoradiograph of a Southern blot of BamH 1 digested *T. flavus* 32908 DNA hybridised with the *A. niger* glucose oxidase gene. Hybridisation performed at 30° C. and the filter washed with 2×SSC at room temperature. Lane 1, *T. flavus* 32908 DNA; lane 2 Hind III digest of $^{32}$P-labelled 1 DNA. The Hind III 1 size markers are shown in kilobases (kb).

FIG. 3 is a schematic outline of glucose oxidase expression cassettes transformed into tobacco. Constructs contain the glucose oxidase gene fused in frame with the carrot root extensin signal peptide (A) or its own glucose oxidase signal peptide (B). Glucose oxidase was placed under control of either the carrot root extensin, TobRB7 or 35S promoter and the 3' end fused to the nopaline synthase (nos) terminator sequence from *A. tumefaciens*. All constructs were cointegrated into the EcoRI site of the binary vector pTAB5 in an indirect orientation to the selectable kanamycin resistance gene. Abbreviations: E, EcoRI; nptll, neomycin phosphotransferase; LB, Left Border; RB, Right Border. Linear maps are not drawn to scale.

FIG. 4 shows in vitro inhibition of *R. solani* growth. Either *A. niger* glucose oxidase or culture filtrate from *T. flavus* 32908 or GOH-1 were incorporated into growth medium and growth of *R. solani* monitored over 38 hours. The glucose oxidase concentration in media containing *A. niger* glucose oxidase and *T. flavus* 32908 filtrate was 0.10 units/ml where one unit+that amount which oxidases 1.0 μmole of β-D glucose to D gluconic acid and $H_2O_2$ per minute at pH 5.1 and 25° C. Standard error was 10–17% of the values obtained (omitted from graph for the sake of clarity).

Figure 5:
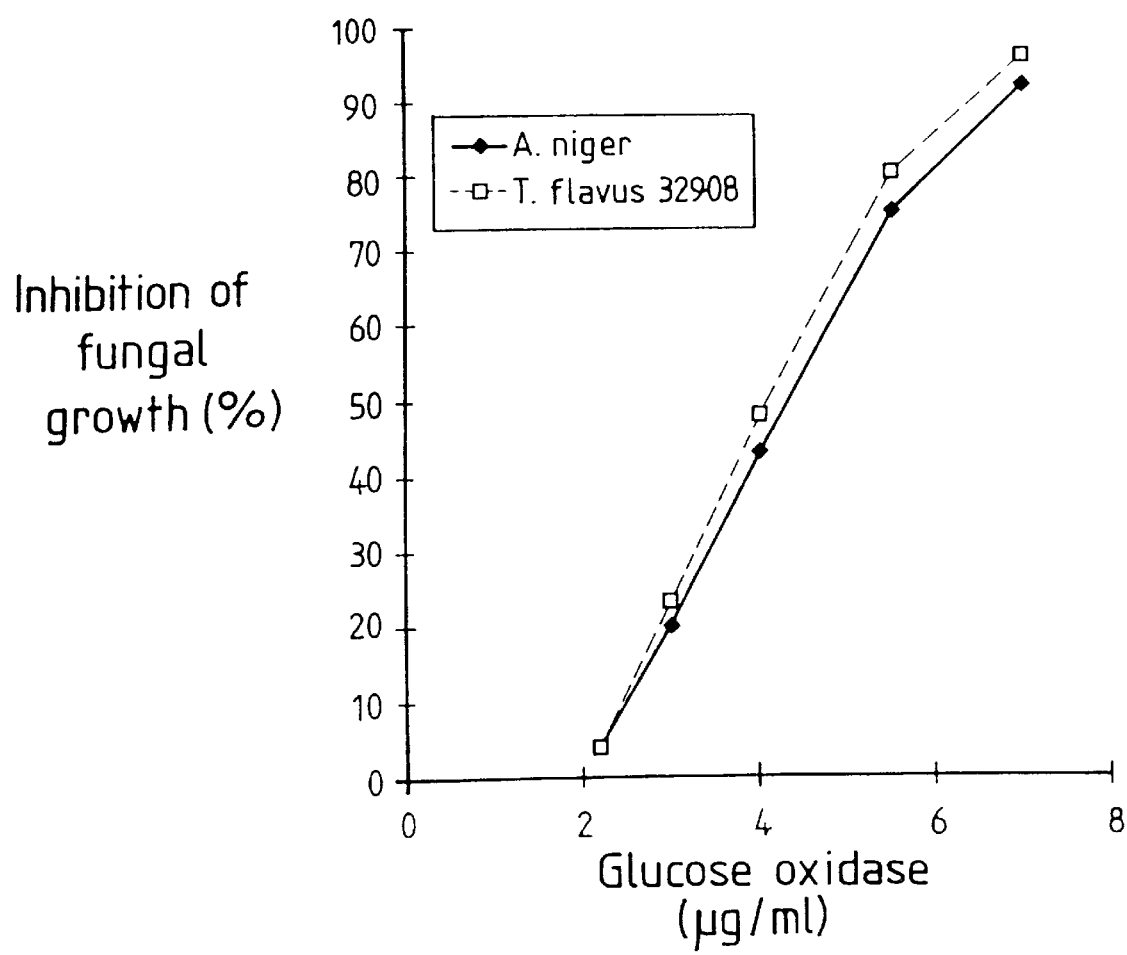

FIG. 5 shows growth inhibition of *R. solani* in different amounts of *T. flavus* culture filtrate and different concentrations of *A. niger* glucose oxidase. The amount of glucose oxidase in the culture filtrate was determined by comparison to standard concentrations of *A. niger* glucose oxidase.

EXAMPLE 1

Fungal Strains

Verticillium fungal isolates were obtained from Dr. S. Allen, Agricultural Research Station, Narrabri. The four isolates (#2, #13, #24, #34) were isolated from cotton in 1990 from farms in different areas.

Three *Talaromyces flavus* strains were obtained from Dr. J. Pitt, CSIRO Food Research. These three strains were:

| | |
|---|---|
| FRR 2268 | ex Brazilian passionfruit concentrate imported into Australia (var macrosporus) |
| FR 2386 | ex Australian passionfruit (var macrosporus) |
| FRR 2417 | ex soil, passionfruit farm, NSW North Coast (var macrosporus). |

Two other *T. flavus* strains were obtained from the American Type Culture Collection (ATCC):

| | |
|---|---|
| ATCC 26015 | ex wood, Japan. |
| ATCC 32908 | ex soil, Japan. |

The *Aspergillus niger* strain from which the glucose oxidase gene was cloned was also obtained from the ATCC: ATCC 9029 ex soil, USA.

An *Aspergillus nidulans* strain was obtained from Dr. M. Hynes, Melbourne University.

Demonstration of the production of glucose oxidase by *Talaromyces flavus* and inhibition of Verticillium growth.

Preliminary experiments were done to confirm that glucose oxidase was being produced by the *T.flavus* (var macrosporus) strains and that this was inhibitory in Australian *V. dahliae* isolates. Initial experiments were performed with the *T. flavus* strains obtained from Dr. J. Pitt. In each case, a spore suspension was transferred to liquid culture medium (potato dextrose+8% glucose), this was maintained at 35° on a rotary shaker for 72 hours. The broth was filtered to remove mycelium and then incorporated 1:1 into double strength Czapeck Dox solution agar. Control plates were made with uninoculated potato dextrose broth. Verticillium mycelial disks were transferred to the plates and radial growth of the developing colonies recorded every 2 days for 8 days. Similar experiments in liquid medium monitored hyphal growth monitored spectrophotometrically as light scattering. No significant reduction in *V. dahliae* growth was observed. Experiments were repeated using the ATCC *T.flavus* isolates. Both cultures proved inhibitory, 32908 more than 26015. This is presumably because 32908 secretes more glucose oxidase and/or less peroxidase scavengers. Inhibition for the 32908 strain is shown in FIG. 1. Glucose oxidase production clearly varies between different isolates of Talaromyces and is not present in the macrosporus biotypes. It was also noted that some *V. dahliae* isolates were more susceptible to inhibition than others.

In order to determine that glucose oxidase was being produced, three different assay systems were used. Two indicator plates were developed for quantitative analysis. Both plates were composed of two layers, the bottom layer in both cases containing potato dextrose+2.5% glucose. The top layer of the first plate contains various mineral salts and calcium carbonate. Gluconic acid produced as a product of glucose oxidase activity dissolves the calcium carbonate resulting in a clear ring around the fungus (Witteveen et al., 1990). The other indicator plate's top layer contains potassium iodide (KI) and starch. Iodine is released from potassium iodide by glucose oxidase and this combines with the starch to form violet-blue zones (Fiedurek et al., 1986). Both ATCC *T. flavus* isolates scored positive in these plate assays while the macrosporus biotypes scored negative.

Quantitative analysis of enzyme activity was performed using a spectrophotometric method. This assays for the production of $H_2O_2$ using reduced O-Dianisidine and Horse Radish Peroxidase. Oxidised O-Dianisidine produced by the reaction is a red colour and can be measured at 400 nm on a spectrophotometer (Fiedurek et al., 1986).

$$\beta\text{-D-Glucose} + O_2 + H_2O \xrightarrow[\text{Oxidase}]{\text{Glucose}} \text{D-Gluconic Acid} + H_2O_2$$

$$\underset{\text{(colourless)}}{H_2O_2 + \text{O-Dianisidine (reduced)}} \xrightarrow[\text{Peroxidase}]{\text{Horse Radish}} \underset{\text{(red colour)}}{\text{O-Dianisidine (Oxidised)} + H_2O}$$

In all cases the *T. flavus* (var macrosporus) strains from Dr. J. Pitt gave negative results. The ATCC strains both tested positive for glucose oxidase production. Strain 32908 produced approximately 15 times more glucose oxidase than strain 26015. This correlates well with the inhibition studies where no significant inhibition was seen with those strains not producing glucose oxidase and inhibition levels were much higher with 32908 than 26015. Assays over time also showed glucose oxidase loses approximately half its activity in 3.5 days. Therefore the increased growth in some of the *V. dahliae* isolates in the later days of the experiment is probably due to inactivation of the glucose oxidase enzyme and a subsequent lowering of $H_2O_2$ concentration.

Cloning of the glucose oxidase gene from *T. flavus*.

Because of the high levels of glucose oxidase produced by the ATCC strain 32908 this was obviously the best choice for the cloning of the gene. The *A. niger* glucose oxidase gene was used as a probe for the isolation of the T. flavus gene as there could be expected to be some homology at the DNA level between the two species. Primers were made to the 5' and 3' ends of the different strands of the *A. niger* coding region. DNA was isolated from *A. niger* strain 9029 using the method of Raeer and Broder (1985) and a polymerase chain reaction (PCR) was carried out using 200 ng of this DNA (Cycle=1 min @ 94° C., 1 min @ 55° C., 3 min @ 72° C.—repeated 35×). The expected 1.8 kilobase (kb) fragment was visualised on a gel and restriction enzyme analysis and sequencing confirmed the fragment as the *A. niger* glucose oxidase gene.

Southern blots of *T. flavus* DNA were then probed with this fragment to determine if the *A. niger* gene was sufficiently similar to the *T. flavus* gene to be used as a probe. Hybridisation was initially carried out at 37° C. (with formamide) overnight and the filter washed twice with 1×SSC, 0.1% SDS at room temperature. As seen in FIG. 2, the *A. niger* gene is clearly visible (16 kb) however only a very faint band was seen in the *T. flavus* lane (2.2 kb). Surprisingly *A. nidulans* which does not produce glucose oxidase also has a faint band present at 3.0 kb. The stringency was reduced in an attempt to increase the *T. flavus* signal. Hybridisation was carried out at 30° C. and the filters washed twice with 2×SSC, 0.1% SDS at room temperature. A band was now clearly visible in the *T. flavus* lane, this was thought to correspond to the glucose oxidase gene. The *A. niger* gene was therefore used under these conditions to screen a *T. flavus* genomic library.

A Sau3A genomic library was constructed in λEmbl 3 using DNA made from *T. flavus* 32908. DNA was partially digested with Sau3A, size fractionated on a glycerol gradient and fragments of 18–22 kb pooled. BamH1 cut Embl 3 arms were purchased from Promega. DNA was ligated into the arms overnight, packaged and then used to infect *E.coli* LE392 cells. A total of 50,000 plaques were obtained, 8,000 were screened and four possible positives isolated. Secondary screening revealed two positives, one stronger than the other. Both were purified, liquid lysates prepared and DNA extracted. They were found to contain inserts of approximately 20 kb.

DNA from the strongest clone was digested with a number of restriction enzymes, blotted and then probed with the *A. niger* gene. Only a single band was highlighted in lanes digested with EcoR1 (7.6 kb) and BamH1 (2.2 kb), therefore these fragments were thought to contain the desired glucose oxidase gene. The fragments were cloned into the plasmid pUC119 and mapped. The 7.6 kb fragment was found to contain the 2.2 kb fragment plus 2.6 kb further upstream and 2.8 kb further downstream. Specific regions were subcloned into M13 and sequenced.

The sequence of the *T. flavus* glucose oxidase gene is set out in Table 2 (SEQ ID NO. 1). The putative signal sequence is underlined. Possible TATM and CMT boxes are double underlined. Translation of the entire sequence is shown beginning at the ATG start site, (nucleotide #1)(SEQ ID NO. 8).

TABLE 2

Sequence of *T. flavus* glucose oxidase gene (SEQ.ID NO:1)

```
-1032
CCACAAGTCCTAGAGAAGACACACAGTCTCGAGCCCAAAGTAAGAATGGATATTGTGACT
-972
TCCTAAAGGCCTCACCGGGCAGTGAGGTATTTGATGTTTACCAAACGCTAGTATGGGTAG
-912
CATAATCGGTGATACCTAGGTATATCATATGTTCATCCACAGGGCTGGGTTTGTGAAGAA
-852
ACTGTAGCACTAGTGCTGCTTAGTTGCATATGGAGTTTCTATCTGCACTATTCCGTTGGA
-792
GGAAGGAAGAAAAGGGCAAGAGAGATACTGTCAAATGAATGTACTCGGGGGTCACTGAAT
-732
ACGTGAAAGCGTACTTAGGTGATCTATTGCGAGAATAGTTCAATGATATCGATGTCCTCT
-672
CGGCGCTCCACTCTCTCTATTCGTATCTGATTCTGATCTGCTCTTCATTCACAACTTTAT
-612
GTATCTGTCATGCCAGTTTTACGAGTACTGGGAAAGTTGGCGCTCAGAGCTGGGATTCTT
-552
GGGTTTCATTGACGCTCAACCTAGAGTTTGAATGATATCGCTTTATCTTTAGATAATCTT
-492
CAACGTAACAATGTGCTTGAGCTTCTAGCGCCAAGATGCGTAGACTTTCGTAAATGGTAG
-432
TTCAAGCTAATAATTCAGGAAAATATTGCAGAGGATTATCGCCACACATGCCGATGGAGC
-372
ATACAGACTCCTCTTGATACGATGCTTTGACCACTCACATCCTCCAGCCTTCCATCCAGG
-312
TCCCTAGGTTCAGCCGTGCTTCCAGCACTTACTGATCAAACCCCTGTAGCACGGCTAGTA
-252
TCTCATATCTTTCCGTCTGCAGCATGAGTCGCTCATGTCTGCACGAGTCCATTTTCAGAA
-192
AGTGGGATAATCTAACCTGGTGGCGAGGCCAAGATACGACATAAAGGAAATGTTTGCTTC
-132
TTGCAAGTCTATAAATTGAGCGACATCTACCGCTGTTCAGACAAGTTCTTCAGCACAACA
-72
ATCAGGTAATTTCACCACTCTCCTTGCAATCCCGTTTATCTTCTCCATCTCCTTGACCTT
-12
               M  V  S  V  F  L  S  T  L  L  L  A  A  A  T  V
GCCGGATCGAAATGGTGTCTGTATTTCTCAGCACTCTTCTTTTAGCCGCGGCTACGGTC
47
    Q  A  Y  L  P  A  Q  Q  I  D  V  Q  S  S  L  L  S  D  P  S
CAAGCCTACCTGCCTGCCCAACAGATTGATGTCCAGTCTAGTCTTCTCAGTGACCCTAGC
107
```

TABLE 2-continued

Sequence of *T. flavus* glucose oxidase gene (SEQ.ID NO:1)

```
         K   V   A   G   K   T   Y   D   Y   I   I   A   G   G   G   L   T   G   L   T
      AAGGTCGCCGGAAAGACCTATGATTACATTATTGCTGGTGGTGGTTTGACTGGCCTTACT
167
         V   A   A   K   L   T   E   N   P   K   I   K   V   L   V   I   E   K   G   F
      GTTGCCGCCAAACTGACAGAAAACCCCAAGATCAAAGTCCTGGTTATTGAAAAGGGCTTC
227
         Y   E   S   N   D   G   A   I   I   E   D   P   N   A   Y   G   Q   I   F   G
      TATGAGTCCAACGATGGAGCCATCATCGAGGATCCAAATGCTTACGGACAAATCTTCGGC
287
         T   T   V   D   Q   N   Y   L   T   V   P   L   I   N   N   R   T   N   N   I
      ACCACTGTTGACCAGAACTACCTCACCGTTCCCCTGATCAACAACCGCACGAACAATATC
347
         K   A   G   K   G   L   G   G   S   T   L   I   N   G   D   S   W   T   R   P
      AAGGCCGGCAAGGGTCTTGGAGGATCAACCTTGATAAACGGTGACTCTTGGACTCGCCCG
407
         D   K   V   Q   I   D   S   W   E   K   V   F   G   M   E   G   W   N   W   D
      GACAAAGTCCAGATTGATTCTTGGGAGAAGGTCTTTGGCATGGAAGGTTGGAATTGGGAC
467
         S   M   F   E   Y   M   K   K   A   E   A   A   R   A   P   T   A   A   Q   L
      AGTATGTTTGAGTACATGAAGAAGGCCGAGGCTGCACGTGCCCCTACTGCTGCTCAACTT
527
         A   A   G   H   Y   F   N   A   T   C   H   G   T   N   G   T   V   Q   S   G
      GCTGCCGGTCACTACTTCAATGCTACCTGCCATGGAACTAACGGTACTGTTCAATCCGGA
587
         A   R   D   N   G   Q   P   W   S   P   I   M   K   A   L   M   N   T   V   S
      GCCCGTGACAACGGTCAACCTTGGTCTCCTATTATGAAGGCCCTTATGAACACCGTCTCG
647
         A   L   G   V   P   V   Q   Q   D   F   L   C   G   H   P   R   G   V   S   M
      GCCCTTGGTGTCCCCGTACAGCAAGACTTTCTCTGCGGTCATCCTCGAGGTGTCTCTATG
707
         I   M   N   N   V   D   E   N   Q   V   R   V   D   A   A   R   A   W   L   L
      ATCATGAACAATGTCGACGAAAACCAAGTTCGTGTTGATGCTGCCCGTGCATGGCTGCTT
767
         P   S   Y   Q   R   P   N   L   E   I   L   T   G   Q   M   V   G   K   V   L
      CCCAGCTACCAGCGCCCCAACTTGGAGATCCTTACTGGTCAGATGGTTGGAAAGGTTCTG
827
         F   K   Q   T   A   S   G   P   Q   A   V   G   V   N   F   G   T   N   K   A
      TTTAAACAGACCGCATCCGGTCCCCAGGCTGTTGGTGTGAACTTCGGTACTAATAAGGCC
887
         V   N   F   D   V   F   A   K   H   E   V   L   L   A   A   G   S   A   I   S
      GTTAACTTTGACGTCTTTGCTAAGCATGAGGTCCTTTTGGCTGCCGGCTCAGCTATCTCT
947
         P   L   I   L   E   Y   S   G   I   G   L   K   S   V   L   D   Q   A   N   V
      CCGCTGATCTTGGAATATTCTGGCATAGGCTTGAAGTCTGTTCTTGATCAGGCCAATGTC
1007
         T   Q   L   L   D   L   P   V   G   I   N   M   Q   D   Q   T   T   T   T   V
      ACTCAGCTTCTTGATCTTCCTGTTGGTATCAATATGCAAGACCAGACCACAACCACTGTC
1067
         S   S   R   A   S   A   A   G   A   G   Q   G   Q   A   V   F   F   A   N   F
      AGTTCCCGTGCTAGTGCCGCTGGTGCTGGTCAGGGTCAGGCCGTCTTCTTCGCCAATTTC
1127
         T   E   T   F   G   D   Y   A   P   Q   A   R   E   L   L   N   T   K   L   D
      ACTGAAACCTTCGGTGACTACGCCCCCCAGGCCAGAGAGTTACTCAACACCAAGCTTGAC
1187
         Q   W   A   E   E   T   V   A   R   G   G   F   H   N   V   T   A   L   K   V
      CAATGGGCTGAGGAGACCGTTGCGCGAGGTGGTTTCCATAATGTAACTGCTCTCAAAGTT
1247
         Q   Y   E   N   Y   R   N   W   L   L   D   E   D   V   A   F   A   E   L   F
      CAATATGAAAACTATCGTAACTGGCTCCTTGACGAAGACGTTGCCTTCGCCGAGCTTTTC
1307
         M   D   T   E   G   K   I   N   F   D   L   W   D   L   I   P   F   T   R   G
      ATGGATACCGAGGGCAAGATCAACTTCGACTTATGGGATCTCATCCCTTTCACTCGTGGT
1367
         S   V   H   I   L   S   S   D   P   Y   L   W   Q   F   A   N   D   P   K   F
      TCCGTCCATATCCTCAGTAGCGACCCTTACCTATGGCAATTCGCCAACGACCCCAAATTC
1427
         F   L   N   E   F   D   L   L   G   Q   A   A   A   S   K   L   A   R   D   L
      TTCCTGAACGAGTTTGACCTCCTTGGTCAAGCCGCTGCTTCCAAGCTTGCTCGTGATCTT
1487
         T   S   Q   G   A   M   K   E   Y   F   A   G   E   T   L   P   G   Y   N   L
      ACCAGCCAAGGTGCTATGAAGGAGTACTTCGCCGGAGAGACTCTTCCAGGATACAACTTG
1547
         V   E   N   A   T   L   S   Q   W   S   D   Y   V   L   Q   N   F   R   P   N
      GTCGAGAATGCTACTCTTTCCCAGTGGTCGGATTATGTCTTACAGAACTTCCGTCCCAAC
1607
         W   H   A   V   S   S   C   S   M   M   S   R   E   L   G   G   V   V   D   A
      TGGCATGCTGTCAGCAGCTGCTCTATGATGTCTAGAGAGCTTGGTGGTGTCGTTGATGCT
```

TABLE 2-continued

Sequence of T. flavus glucose oxidase gene (SEQ.ID NO:1)

```
1667
 T   A   K   V   Y   G   T   Q   G   L   R   V   I   D   G   S   I   P   P   T
ACTGCCAAGGTGTACGGTACGCAGGGCCTACGTGTCATTGATGGCTCTATTCCTCCGACT
1727
 Q   V   S   S   H   V   M   T   I   F   Y   G   M   A   L   K   V   A   D   A
CAGGTGTCTTCTCATGTCATGACCATTTTCTACGGAATGGCTTTGAAAGTTGCTGATGCG
1787
 I   L   D   D   Y   A   K   S   A   *
ATTCTGGACGACTATGCCAAAAGTGCCTAGAGGTGTCATGAATCGCGGTTCGTCAGCGAA
1847
TTTGCTAGGGTTTAGATCACCGATTTTTTCTCCTCGCTCATACATTGTTAGATTCTCGCA
1907
CATATAGATCGATTTAAATTGCTTATAGACAACGTGAAATTTACTACTTATTCATCGAAC
1967
TTACATTCTTCAAAATATTCAAGAGAGCTC
```

Approximately 3.0 kb of T. flavus DNA has been sequenced on both strands. Analysis has revealed a 1815 bp open reading frame (ORF) from bas 1032 to base 2847, (Table 2). This ORF is exactly the same size as the A. niger glucose oxidase open reading frame and is 65% homologous to it at a nucleotide level. Comparisons show that the T. flavus gene has undergone an insertion at bases 1089 to 1091 of a leucine amino acid and a deletion at bases 1349 to 1351 of a glutamic acid residue. At an amino acid level the T. flavus gene is 64% homologous to the A. niger glucose oxidase protein (77% similarity). Hydrophobicity plots of the two proteins show them to be very similar. Like the A. niger ORF, T. flavus contains a putative secretion signal sequence at the beginning of the ORF. This sequence seems to extend for approximately 20 amino acids and consists predominantly of hydrophobic amino acids. All this strongly suggests that ORF corresponds to the coding region of the T. flavus glucose oxidase gene.

As no conserved regions have been clearly defined for fungal untranslated flanking regions it is difficult at this stage to define essential sequences in these regions. There is a possible TATM sequence at −122, and two CMT boxes are present at −43 and −73 (wrt to the ATG initiation codon). The CMT boxes are within a very pyrimidine rich region (74%) which spans from −12 to −73 bases upstream. Such regions have been found in many fungal promoters and may be important in positioning the site of transcription initiation (Hammer and Timberlake, 1987). No MTAAA polyadenylation sequence has been found. This 3' region is however quite AT rich, 64%. This compares with 50% for the coding region and 55% for the 5' untranslated region.

Demonstration of Glucose Oxidase activity on the cloned DNA sequence.

As all of the macrosporus biotypes of the T. flavus were not producing glucose oxidase these were useful recipients to demonstrate that the cloned gene was indeed functional. A transformation procedure for T. flavus had to be developed to allow the introduction of the glucose oxidase gene into one of these strains. Such transformants could also be tested for their antagonistic properties towards V. dahliae to further characterise the role glucose oxidase in the mycoparasite relationship between these organisms. Additionally, some of the transformants may be better glucose oxidase producers than 32908 and could be useful as biocontrol agents (strain 32908 may not be able to be used in the field because of quarantine regulations).

Many different filamentous fungi have now been transformed although the frequencies reported are often very low when the protoplast method is used. In this method the cell wall is digested away in the presence of an osmotic stabiliser to produce spheroplasts. These are exposed to DNA in the presence of $CaCl_2$ and polyethylene glycol (PEG) which promote DNA uptake. Following treatment, the spheroplasts are allowed to regenerate in an osmotically stabilised medium at which time selective pressure is applied. The basic procedure followed is that of Murray et al., 1992. The recipient strain used was FRR 2417 as this had been obtained from Australian soil. Preliminary experiments showed this strain to be sensitive to moderate concentrations of hygromycin, (200 $\mu$g/ml) so initial transformations were done with the vector pAN7-1 (Punt et al., 1987) which carries the gene for hygromycin resistance under the control if A. nidulans 5' and 3' sequences. Before transformation the vector was linearised with HindIII as linear DNA is thought to be more recombinogenic than circular DNA (Orr-Weaver et aL, 1981).

Hygromycin resistant colonies were observed 1–2 weeks after transformation. Approximately 20 transformants/$\mu$g of DNA were obtained. This corresponds to a transformation frequency of about 0.001% of the original number of protoplasts or 0.01–0.02% if one takes into account that only 5–10% of the protoplasts regenerate after incubation in PEG. Southern blotting and probing of transformant DNA with pAN7-1 confirmed the presence of the hygromycin gene in the fungal genome. Size and number of fragments hybridizing differs from transformant to transformant. As DNA was cut with EcoRV, an enzyme which does not cut within the vector, hybridizing fragments represent one copy or several tandem repeats of the vector. Differences in fragment size are therefore caused by integration of the vector into different places in the fungal genome. Multiple fragments arise when the vector integrates into a number of different sites in the transformant genome.

The 7.6 kb EcoR1 fragment believed to contain the T. flavus glucose oxidase gene was cotransformed into FR 2417 with pAN7-1. Transformants were initially selected on hygromycin and then these colonies screened on both indicator plates. A similar transformation frequency was obtained, (0.01%). Of 29 transformants analysed, 18 were glucose oxidase positive and 11 negative, i.e. a cotransformation frequency of 62% and clearly demonstrated that the 7.6 kb EcoR1 fragment contained a functional T. flavus glucose oxidase gene.

Glucose oxidase expressed in a non-producing strain is toxic to Verticillium.

Talaromyces flavus var macrosporus is a non-glucose oxidase producing strain that has no antagonistic activity against fungi such as Verticillium. Transgenic macrosporus strains expressing the cloned glucose oxidase gene were tested for antifungal effects using culture filtrates as described in FIG. 1. The transformed fungi produced copious amounts of glucose oxidase and this proved toxic to Verticillium (FIG. 1), although the growth suppression was not quite as large as for the native glucose oxidase producing strain, perhaps indicating that there may be some other components to the growth inhibition. This strain has yet to be tested for biocontrol properties in vivo.

EXAMPLE 2
Glucose Oxidase is toxic to insect larvae.

H. armigera larvae can be reared on a synthetic medium containing soybean flour, wheat germ, yeast and various vitamins and oils. When glucose oxidase (from Aspergillus niger, Sigma Co.) was incorporated into the diet at 1 mg/ml it did not affect larval growth or survival except when glucose (8% w/v) was also present (Table 3) when assessed after 7 days.

TABLE 3

Effect of glucose oxidase on larval survival and growth.

| Treatment | Survivors | Average Wt (mg) | Wt % of Control |
|---|---|---|---|
| Control (added water) | 10/12 | 10.5 | 100 |
| Control + Glucose oxidase | 11/12 | 8.4 | 80 |
| Control + Glucose oxidase + Glucose | 0/12 | 0 | 0 |
| Control + Glucose | 9/12 | 2.8 | 27 |
| Control + Sucrose | 9/12 | 2.6 | 25 |
| Control + Sucrose + Invertase | 12/12 | 2.5 | 24 |
| Control + Sucrose + Invertase + Glucose Oxidase | 7/12 | 0.7 | 6.6 |

No survivors were present in the glucose oxidase plus glucose treatment whereas all other treatment had significant numbers of survivors out of the 12 larvae tested. Surprisingly some of the control treatments with sugars had some effects on growth rates perhaps because of greater bacterial or fungal growth in the medium. Glucose generated by the action of yeast invertase (1 mg/ml) on sucrose could partially substitute for glucose added to the medium although this was not sufficient to kill all of the insects. Similar results were obtained on two separate occasions.

EXAMPLE 3
Expression of T. flavus glucose oxidase in transgenic plants.
MATERIALS AND METHODS
Gene constructions.

Glucose oxidase plasmids

All DNA manipulations were performed using standard procedures (Sambrook et al., 1989). A 2.2 kb Pst/SacI fragment containing the *T. flavus* glucose oxidase open reading frame in addition to approximately 250 bp of 5' and 150 bp of 3' DNA was subcloned into pBluescript $SK^-$ (Stratagene) to create pGO. The 4 kb EcoRI DNA fragment from PDC5A1 was recloned into the EcoRI restriction site of pJKKm creating pDC5A2. Restriction mapping revealed a KpnI site approximately 3 kb downstream from the 5' EcoRI site of the extensin fragment. This 3 kb KpnI fragment from PDC5A2, was subcloned into pBluescript $SK^-$ to create pEx. In vitro mutagenesis was carried out with either pGO1 or pEx to introduce restriction enzyme recognition sites around the ATG and 3' end of the putative secretion signal peptides of both genes. The presence of the correct mutations was confirmed by restriction digest analysis. The following synthetic oligonucleotides were used:

| | | |
|---|---|---|
| G01 | CCTTGCCGACTAGTA<u>ATG</u>GTGT | (SEQ ID NO:2) |
| G02 | CCTACCTGGATATCCAACAGAT | (SEQ ID NO:3) |
| Ex1 | TTGGTTGTACTAGTC<u>ATG</u>GGAA | (SEQ ID NO:4) |
| Ex2 | CCACAGCTGTTAACACTTACTC | (SEQ ID NO:5) |

The following plasmids were created, pGO-1, which had a SpeI site introduced just prior to the initiating ATG of the *T. flavus* glucose oxidase gene; pGO-2, which had an EcoRV site introduced at the 3' end of the putative *T. flavus* glucose oxidase signal peptide; pEx-1, which has a SpeI site introduced just prior to the initiating ATG of the carrot extensin gene; pEX-2, which has a HpaI site introduced at the 3' end of the putative carrot root extensin signal peptide and a Spel site introduced just prior to the initiating ATG of the extensin gene.

Plasmid pFGOEN

The SpeI/SacI DNA fragment from pGO-1 containing the glucose oxidase gene and 5' signal peptide was subcloned into pBluescript SK– to create pGO-1A. The SpeI/EcoRI fragment from pEx-1 was cloned into the SpeI/EcoRI restriction sites upstream of the glucose oxidase gene in pGO-1A to create pFGOE. The EcoRI/SacI fragment from pFGOE containing the glucose oxidase gene and signal peptide fused to the extensin promoter was then subcloned into the EcoRI/SacI restriction sites of pGN 100 (Bogusz et al., 1990) to create PFGOEN-1.

Plasmid pEGOEN

The 2.2 kb PstI/SacI fragment from pGO2 containing the glucose oxidase gene into which HpaI restriction site had been engineered, was subcloned into the pstI/Sacl restriction sites in pJKKm (Kirschman and Cramer, 1988). This plasmid was digested with EcoRV/EcoRI and the 1.9 kb fragment containing the glucose oxidase gene cloned into pBluescript $SK^-$ to create pGO2A. To create PEGOE, the 0.75 kb HpaI/KpnI DNA fragment from pEx-2 containing the extensin promoter and secretion signal peptide was subcloned into the EcoRV/EcoRI restriction sites upstream of the glucose oxidase gene in pGO2A. The EcoRI/SacI fragment from pEGOE containing the extensin promoter, signal peptide and glucose oxidase gene was then subcloned into the EcoRI/SacI restriction sites of pGN100 to create pEGOEN.

Plasmid pFGOTN

The TobRB7 promoter was subcloned into pBluescript $SK^-$ to create pTobRB7–2. To create pFGOTN, the extensin promoter in pFGOEN was relaced with the pTobRB7 promoter by cloning the SpeI/EcoRI fragment from pTobRB7-2 into the SpeI/EcoRI restriction sites of pFGOEN.

Plasmid pEGOTN

The plasmid was created by replacing the SpeI/EcoRI extensin promoter fragment from pEGOEN with the SpeI/EcoRI TobRB7 promoter fragment from pTobRB7-2.

Plasmid PFGOSN

The PstI/BamHI DNA fragment from 35SKNΔBam (J. Walker, unpublished) containing the 35S promoter was sucloned into the PstI/BamHI restriction sites in pBluescript $SK^-$ to create p35S-1. Plasmid pFGOSN was created by replacing the SpeI/EcoRI extensin promoter fragment in pFGOEN with the SpeI/EcoRI DNA fragment from p35S-1.

Plasmid pEGOSN

The EcoRI/SpeI fragment from pEGOEN containing the extensin promoter was replaced with the EcoRI/SpeI fragment from p35S containing the 35S promoter.

Gene fusions occurring within an open reading frame were checked by dideoxy sequencing using a Pharmacia T7 sequencing kit to ensure the correct open reading frame was conserved. All of the above plasmids were linearized with EcoRI and cointegrated into the binary vector pTAB5 in the opposite orientation to the selectable kanamycin gene. Triparental mating was employed to transfer the binary vector constructs to the super-virulent disarmed Agrobacterium tumefaciens strain AGL1 (Lazo et al., 1991) and constructions were verified by restriction enzyme analysis.

Plant transformations.

Transformation of N. tabacum (Wisconsin 38) using A. tumefaciens was performed as described in Lyons et aL., (1989). Plants were subcultered every 6–8 weeks to fresh MS medium containing 3% sucrose and 0.8% agar. Seed from Gossypium hirsutum (cv Coker 315) were surface sterilized and transformed as described in Cousins et al (1991) with the following modifications. After 2 days co-cultivation with the appropriate A. tumefaciens strain each explant was transferred to callus initiation media containing 50 mg/l kanamycin. Six weeks later callus was subcultered to the same media containing 25 mg/l kanamycin. After a further six weeks surviving callus was subcultered to solidified basal medium containing no hormones or antibiotics. Embryos formed 5–12 weeks later, large embryos forming roots were transferred to deep petri dishes containing Stewart and Hsu (1977) medium solidified with Phytogel and magnesium chloride.

Analysis of plant tissue for the presence of glucose oxidase.

Glucose oxidase activity was assayed qualitatively by submerging small pieces of plant tissue in KI/starch stain. Tissue was incubated overnight at room temperature before being scored for activity. For quantitative glucose oxidase assays, leaf or root tissue removed from plants propagated in tissue culture, was homogenized with 0.1M $Na_2PO_4$ buffer (pH 6.0) in a mortar and pestle. Homogenate was poured into eppendorf tubes and centrifuged at 13000 rpm for 15 minutes. The supernatant was removed and incubated at 4° C. for 2–3 hours before it was assayed for the glucose oxidase activity. Protein concentration was determined by the method of Bradford (1976) and measured using a Labsystems Multiskan Plus.

PCR reactions.

Isolation of Genomic DNA

Genomic DNA was isolated from young leaves of tobacco plants propagated in tissue culture. One leaf was homogenized in an eppendorf tube containing 300 μl of grinding solution (comprised of 1.25 ml of TE3D buffer, (0.02M Tris, 002M $Na_2EDTA$, 1% Nonadet P40, 1.5% lithium dodececyl sulphate and 1% sodium deoxycholate) 2.5ml of equilibritated phenol and 50 μl of β-mercaptoethanol). After homogenization, 250 μl of ammonium acetate/EDTA solution (3M ammonium acetate, 0.4 mM $Na_2EDTA$, 0.18M NaOH) and 400 μl of chloroform was added and the tube mixed for 20 minutes. The tube was centrifuges at 13000 rpm at 4° C. for 10 minutes, the supernatant removed and DNA precipitated by the addition of 0.6 volumes of isopropanol. The pellet was resuspended in TE buffer and treated with Ribonuclease A (previously boiled) then extracted with phenol/chloroform, ethanol precipitated and resuspended in distilled water.

PCR conditions

The following oligonucleotide primers which are complementary to two regions in the T. flavus glucose oxidase open reading frame (position 681 and 1513 with respect to the initiating ATG) were synthesized on an Applied Biosystems DNA synthesizer.

```
                              (SEQ. ID NO:6)
FMGO3A     5' GCGGTCATCCTCGAGGTGTCTCTATG 3'

(SEQ. ID No:7)
GOFMR      5' TACTCCTTCATAGCACCTTGGCTGGT 3'
```

PCR was carried out using either 250 ng of tobacco genomic DNA or 40 ng of pEGOSN plasmid DNA and Taq DNA polymerase buffer (Promega); 2.5 mM $MgCl_2$; 200 μM each dNTP; 1 μM each primer and 2.5 units of Taq DNA polymerase (Promega). The reaction consisted of 30 cycles:

cycle 1=5 min @ 94° C., 2 min @ 55° C., 2 min @ 72° C. (performed once)

cycle 2=1 min @ 94° C., 1 min @ 55° C., 2 min @ 72° C. (performed 29 times)

cycle 30=5 min @ 30° C. (performed once)

PCR reaction products were visualized by running the completed reaction on a 0.7% agarose gel.

Northern analysis.

Total RNA was extracted from young tobacco leaves excised from plants being propagated in tissue culture using the method of Dolferus et al (1994). Equal amounts (20 μg) of total RNA was loaded on 1.1% agarose gels containing 2.2M formaldehyde in the presence of ethidium bromide. After electrophoresis the gels were transferred and UV cross-linked onto Hybond-N nylon membranes (Amersham). The plasmid pGO-1A which contained the entire T. flavus glucose oxidase open reading frame was used to generate a riboprobe to detect glucose oxidase RNA. This plasmid was linearized with EcoRI and an antisense [$^{32}$P] UTP-labelled riboprobe was made using T3 polymerase and a Promega in vitro transcription kit. An antisense riboprobe corresponding to an Arabdopsis ubiquitin clone (Burke et al., 1988) was used to quantitate the amount of tobacco RNA. RNA probe hybridizations and washing of filters was carried out as described in Dolferus et al (1994). Filters were exposed to X-ray film at $^-80°$ C. for 2–3 days. Analysis and quantitation of the hybridization signals was performed with a phosphorimager (Molecular Dynamics, Sunnyvale, Calif.).

RESULTS

Construction of plasmids for the expression of T. flavus glucose oxidase in plants.

As the glucose oxidase gene isolated was of fungal origin, it was not known if the secretion signal peptide at the 5' end of the gene would function correctly in plants. To obtain good gene expression, the presence of a functional signal peptide was thought to be important for two reasons. First, glucose oxidase is glycosylated protein, lack of glycosylation caused by a nonfunctional signal peptide could decrease enzyme activity. Secondly, because of the potential toxicity of the hydrogen peroxide produced by glucose oxidase, it would be desirable to have the enzyme excreted from the cell. The effect replacing the fungal signal peptide with one from plants has on glucose oxidase gene activity is not known. Such a substitution could decrease gene expression and or protein activity. To avoid these potential problems, two different series of expression vectors were made. In the pFGO series, the glucose oxidase secretion signal peptide was retained. In the pEGO series, the final signal peptide was replaced with the secretion signal peptide from the carrot extensin gene (Chen and Varner, 1985) as described in Material and Methods. This plant signal peptide was used, as a similar extensin signal peptide from tobacco has been shown to mediate the secretion of neomycin phosphotransferase II (nptII) from tobacco protoplasts (Loose et al., 1991).

In order to successfully express the glucose oxidase gene plants, root specific or inducible gene expression may be necessary because of the potential toxicity of the hydrogen peroxide to the plant. The glucose oxidase gene and signal peptide from each of these plasmids was therefore joined to three different promoters as described in Materials and Methods. The promoters used were the 35S promoter from cauliflower mosaic virus, the TobRB7 promoter from tobacco (Yamamoto et al., 1991) and the extensin carrot root promoter (Chen and Varner, 1985). Each of these promoters directs a different pattern of gene expression in plants. The 35S promoter constitutively expresses genes in most plant tissues (Odell et al., 1985), TobRB7 directs constitutive, root specific gene expression (Yamamoto et al., 1991) and the extensin carrot root promoter has been shown to be wound inducible in carrot roots (Chen and Varner, 1985).

As described in Materials and Methods, each construct was fused to a NOS 3⁻ terminator and then cloned into the EcoRI site of the binary vector pTAB5 (Tabe et al., 1995). Restriction enzyme analysis was performed on all constructs to confirm the correct integration and orientation of the glucose oxidase gene in the binary vector (results not shown). Constructs containing the glucose oxidase gene in an indirect orientation to that of the 35S-nptII gene (kanamycin resistance) were introduced into tobacco by way of Agrobacterium-mediated transformation. Diagrams of the plasmids, pEGOE (carrot root extensin promoter), pEGOT (pTobRB7 promoter) and pEGOS (35S promoter) are shown in FIG. 3. These constructs all contain the extensin secretion signal peptide. The three constructs containing the glucose oxidase secretion signal peptide attached to the glucose oxidase gene (pFGO series) are also shown and are identical to the pEGO series except that they have the glucose oxidase secretion signal peptide instead of the extensin secretion signal peptide.

Expression of *T. flavus* glucose oxidase in *Nicotiana tabacum*.

For each of the six constructs, fifteen to twenty transgenic tobacco plants were regenerated. Glucose oxidase activity in transgenic plants was assayed qualitatively by submerging small pieces of plant tissue into a solution of glucose, potassium iodide, (KI) and soluble starch. In transgenic plants expressing functional glucose oxidase, hydrogen peroxide produced by glucose oxidase, oxidises the KI to iodine ($I_2$). The $I_2$ then interacts with the starch to form a blue-black starch complex. The presence of glucose in the strains solution was not necessary for the formation of the blue-black colour but its presence did greatly increase speed of colour formation. A similar solution has been used by Olson and Varner (1993) and Schopfer (1994) to detect endogenous hydrogen peroxide in plant tissue. However, when tissue is completely submerged in stain solution (anaerobic conditions) no endogenous activity is detected. This stain solution can therefore be used under these conditions to assay for glucose oxidase activity.

As seen in Table 4, glucose oxidase activity could be detected in only three of the sixty tobacco plants obtained from transformation with constructs in which the glucose oxidase gene retained its own secretion signal peptide (pFGO series). Very weak staining was observed in all three transformants so the glucose oxidase activity in these transformants is thought to be very low. Many of the plants (58%) obtained from transformation with constructs containing the glucose oxidase gene attached to the extensin secretion signal peptide (pEGO series) did show glucose oxidase activity. In particular, 80% of the plants transformed with constructs in which the glucose oxidase gene was driven by the 35S and TobRB7 promoter showed activity.

TABLE 4

Glucose oxidase activity in transgenic tobacco transformed with different constructs. All plants are believed to be independent transformants. Activity was determined qualitatively using a KI/starch solution. Each plant was tested three times, the results were identical each time.

| Construct used to transform W38 Tobacco | Number of positive transgenic plants in KI stain |
|---|---|
| pEGOS | 13/15 |
| pEGOT | 11/15 |
| pEGOE | 2/15 |
| pFGOS | 3/20 |
| pFGOT | 0/20 |
| pFGOE | 0/20 |
| Untransformed W38 | 0/5 |

Analysis of glucose oxidase expression in T1 progeny.

To obtain plants for further analysis, plants expressing the glucose oxidase gene controlled by the 35S and TobRB7 promoter (pEGOS and pEGOT constructs) were potted in soil and transferred to the glasshouse where they were propagated further. In soil, all plants appeared to grow normally and all plants produced flowers and pollen. Seeds were obtained from all plants containing plasmid pEGOT. Only six of the ten plants containing the glucose oxidase gene controlled by the 35S promoter (pEGOS) produced seed. Compared to W38 untransformed plants, four of these six plants, had small seed pods which contained few seeds. The other two plants produced seed pods containing a similar number of seeds and of similar size to seed pods produced by untransformed W38 tobacco plants.

Seeds from eleven of the transgenic plants were surface sterilized and germinated on agar medium. To detect glucose oxidase activity, seedlings from each plant were stained with KI solution. Some localization of gene expression was seen, staining occurs over the entire seedling in seedlings containing pEGOS but is confined to the root in seedlings containing pEGOT.

Thirty seedlings from each plant were randomly chosen and scored for glucose oxidase activity by staining with KI/starch solution (Table 5). It was not possible however, to determine whether seedlings were homozygous or hemizygous for the glucose oxidase gene using this method. Except for seedlings from plant GOS-13, glucose oxidase activity was detected in approximately 75% of the seedlings from each plant (Table 5). Approximately 96% (29/30) of the seedlings from GOS-13 tested displayed glucose oxidase activity. Seeds were also germinated one medium containing kanamycin and scored for survival (Table 5). Three percent of GOS-13 seedlings and approximately 25% of the other seedlings tested germinated bleached and later died. Therefore, in most plants the glucose oxidase and kanamycin resistance gene segregates in a Mendilian 3:1 ratio. The higher frequency of the glucose oxidase and kanamycin resistance gene in GOS-13 progeny could result if the T-DNA has integrated into two different loci. In this situation only $\frac{1}{16}$ seedlings (approximately 6%) would be expected to not have glucose oxidase activity. The occurrence of two different integration events could also result in the high level of glucose oxidase activity found in GOS-13.

TABLE 5

Inheritance of the glucose oxidase and kanamycin resistance gene in T1 transgenic tobacco seeds. a: Seedlings were stained with KI/starch solution to determine glucose oxidase activity. b: Seedlings were germinated on media containing 100 µg/ml kanamycin to determine presence of nptII gene.

| Plant | Percentage of T1 seedlings producing glucose oxidase.[a] (of 30 scored) | Percentage of surviving T1 seedlings.[b] (of 30 scored) |
|---|---|---|
| EGOS-9 | 77 | 73 |
| EGOS-13 | 97 | 97 |
| EGOS-24 | 73 | 83 |
| EGOT-2 | 80 | 83 |
| EGOT-9 | 73 | 70 |
| EGOT-10 | 67 | 77 |
| EGOT-15 | 67 | 83 |
| EGOT-17 | 83 | 70 |
| EGOT-18 | 67 | 73 |
| EGOT-19 | 80 | 70 |
| EGOT-21 | 73 | 83 |

Expression of glucose oxidase in *Gossipium hirsutum*.

Plasmids pEGOT (Glucose oxidase gene driven by the TobRB7 promoter and extensin signal peptide) and pEGOE (glucose oxidase gene driven by the extensin promoter and extensin signal peptide) were separately transformed into *G. hirsutum* cv. Coker by way of Agrobacterium mediated transformation. Calli was selected from each of the transformations on kanamycin containing medium and regenerated into plants as described in Materials and Methods.

Approximately 50% of the callus derived from tissue transformed with pEGOE died 3–4 months after the transformation however 16 plants from independent transformation events were still regenerated. 34 plants from independent transformation events were regenerated after transformation of cotton with pEGOT. Roots from at least three clones of each line were tested for glucose oxidase activity in KI/starch stain solution before being transferred to the pots in the glasshouse. Three of the 16 lines regenerated after transformation with pEGOE and 23 of the 34 lines generated after transformation with pEGOT produced glucose oxidase (Table 6).

Plants were placed into different groups depending on the time taken for the KI/starch stain solution to completely change colour after the addition of roots to the solution. Group 1 roots completely changed the colour of the stain solution within one hour of being added to the solution, Group 2 within four hours, Group 3 overnight and Group 4 never completely changed the colour of the solution but some staining of solution and roots was observed (Table 6). Glucose oxidase activity ranging from weak to strong is seen in cotton plants transformed with pEGOT. Only very weak activity is seen in cotton plants transformed with pEGOE.

All sixteen cotton lines regenerated after transformation of cotton with pEGOE and the 23 lines regenerated after transformation with pEGOT which are expressing glucose oxidase are being progated further in the glasshouse. To date, six lines containing pEGOT have flowered, self pollinated and set seed (Table 6).

TABLE 6

Regenerated cotton lines producing glucose oxidase. Each line is believed to represent an independent rransformatikon event. Cotton lines were placed into different groups based upon the time taken for three 2 cm roots to completely change the color of 250 µl of KI/ starch solution.

| | Regenerated cotton lines producing glucose oxidase. | Total number of plants in group. |
|---|---|---|
| Plants containing pEGOT | | |
| Group 1 | T-53, T-76*, T-78, T-97 | 4 |
| Group 2 | T-2*, T-10, T-12, T-13, T-24*, T-52, T-71, T-77, T-90, T-92*, T-105 | 11 |
| Group 3 | T-5, T11, T-14*, T-16, T-68* | 5 |
| Group 4 | T-48*, T-99, T-19 | 3 |
| Plants containing pEGOE | | |
| Group 1 | — | 0 |
| Group 2 | — | 0 |
| Group 3 | — | 0 |
| Group 4 | E-42, E-60, E-91 | 3 |

*Indicates those lines which have flowered and formed bolls.

EXAMPLE 4
Resistance of transgenic tobacco plants expressing glucose oxidase to *Rhyzoctonia solani*.

Australian isolates of *V. dahliae* do not infect tobacco so the glucose oxidase producing transgenic tobacco plants described in Example 3 could not be tested for increased resistance to verticillium wilt. Another soil borne fungus, *Rhyzoctonia solani* has been found to be susceptible to low concentrations of hydrogen peroxide by Kim et al., 1990[a,b]. This fungus infects many different plant species including tobacco and usually invades the hypercotyl of young seedlings where it decays stem tissue eventually causing the seedling to collapse. The pathogen is not a major problem in agriculture as it is readily controlled by fungicides or as cool, wet conditions early in growing seasons have been found to favour disease development, losses can be greatly reduced by delayed planting.

An Australian isolate of *R. solani* originally isolated from cotton was found to infect W38 tobacco under favourable conditions, and this isolate has been tested for its tolerance to glucose oxidase and found to be moderately sensitive to the enzyme. To determine if plants expressing glucose oxidase are resistant to *R. solani* infection, T1 tobacco seedlings expressing the *T. flavus* glucose oxidase gene under control of either the 35S or TobRB7 promoter are tested for increased ability to survive in sand infested with the *R. solani* isolate.

MATERIALS AND METHODS
Fungal Isolates.

A *R. solani* isolate previously isolated from cotton was kindly supplied by Dr. Michael Priest, NSW Department of Agriculture, Rydalmere, Australia. The *T. flavus* and *V. dahliae* strains used are described above.

*R. solani* infection trials.

Tobacco seeds (Wisconsin 38 and transgenic derivatives) were surface sterilised by placing seeds in 70% ethanol for 1 minute and then transferring to a 10% bleach solution containing 1 drop/100 ml of Tween 20 for 10 minutes. After washing five times with sterile distilled water, seeds were placed on MS media containing 100 µg/ml kanamycin and germinated in the light at 26° C. R. solani was grown at 26°

C. on potato dextrose agar for 7 days. Mycelium was removed from plates with a spatula and blended with sterile nutrient solution (Hoagland No.2 solution (Hewitt, 1966) and 0.5% glucose) for 30 seconds in a Waring blender. Mycelial fragments were filtered through 2 mm nylon mesh before being counted with a "Weber Scientific" counting chamber. Sand (300 ml) was previously dispensed into containers (13cm×11cm) and autoclaved twice. *R. solani* mycelial fragments were mixed with nutrient solution and the solution poured evenly over sand in the containers ($4 \times 10^8$ mycelial fragments/container). 21-day-old tobacco seedlings were removed from agar and planted directly into the sand. Containers were covered with clingwrap and placed in an "Environ Air" growth cabinet for 5–6 weeks (24° C., 12 hours light; 20° C., 12 hours dark). Seedlings were removed from sand, washed in water and blotted dry on blotting paper. After weighing, a small mount of tissue was placed in KI/starch stain to test for glucose oxidase production.

RESULTS

Effect of glucose oxidase on the growth of *Rhyzoctonia solani*.

Glucose oxidase was examined in vitro for its ability to inhibit the growth of an Australian isolate of *R. solani*. Different concentrations of *A. niger* glucose oxidase suspended in potato dextrose broth and different amounts of filtrate from *T. flavus* 32908 and GOH-1 were inoculated with *R. solani* and fungal growth was monitored using a microtitre plate reader. Duplicates were performed for each experiment and the experiment was repeated twice.

As shown in FIG. 4, filtrate from *T. flavus* 32908 broth and broth containing *A. niger* glucose oxidase were found to significantly inhibit *R. solani* growth. The growth profile of *R. solani* in PD broth alone, PD broth plus gluconic acid or in filtrate from GOH-1 was very similar indicating that as in *V. dahliae*, it is the hydrogen peroxide produced by glucose oxidase which is toxic to *R. solani*. Growth inhibition curves for *R. solani* were calculated 26 hours after the start of fungal growth (FIG. 5). Approximately 4.4 µg/ml of *A. niger* glucose oxidase and the equivalent of 4.1 µg/ml of glucose oxidase in *T. flavus* 32908 filtrate was required to inhibit *R. solani* growth by 50% ($IC_{50}$). These values are approximately twice the glucose oxidase $IC_{50}$ value determined for *V. dahliae* (2.2 µg/ml).

Infection of transgenic tobacco plants expressing glucose oxidase with *R. solani*.

Seedlings from several of the tobacco plants found to express glucose oxidases (GOS-9, 13, 24 and GOT-9, 10, 21) and seedlings from a 35SGUS control were surface sterilised and germinated on growth media containing kanamycin. Three weeks later, seedlings homozygous or hemizygous for the kanamycin resistance gene were transferred to sand infested with *R. solani* to determine their susceptibility to fungal attack. As a control, seedlings were also transferred to sand containing no *R. solani*. The sand in both experiments was previously moistened with sterilised Hoagland's solution containing 0.5% glucose, the presence of glucose in the solution was necessary to promote fungal infection. After 38 days seedlings were assessed for fungal infection and surviving seedlings tested for glucose oxidase activity with KI/starch solution.

Seedlings were too small to reisolate fungus from to confirm infection by *R. solani* but symptoms typical of *R. solani* infection (rotting of hypocotyl and slow growth) were observed only when seedlings were grown in sand infested with *R. solani*.

All surviving seedlings except those from 35 GUS tested positive for glucose oxidase activity. When grown in sand under control conditions, 85–100% of all seedlings survived. When grown in infested sand, only 45% of 35SGUS seedlings survived whereas 65–100% of seedlings producing glucose oxidase survived. The 35SGUS seedlings grown in infested sand weighed on average 47% less than 35SGUS seedlings grown under control conditions (Table 7). Little difference in average seedling weight was observed between glucose oxidase expressing seedlings grown in infested or uninfested sand.

Of the glucose oxidase producing seedlings tested, those from GOT-21 seemed to be most susceptible to fungal infection. Only 65% of the seedlings survived when grown in infested sand and the weight of these seedlings on average was slightly lower (80%) than the weight of GOT-21 seedlings grown under control conditions. No significant difference in weight and percentage survival was found among the other glucose oxidase producing seedlings tested. As GOT-21 produces the least amount of glucose oxidase among the transformants tested, this suggests there is a correlation between the level of glucose oxidase activity and resistance to *R. solani*.

TABLE 7

Average fresh weight of surviving transgenic seedlings after 38 days growth in sand either infested or uninfested with *R. solani* ($4 \times 10^8$ propagules/tray). Twenty seedlings from each transformant were planted in the experiment.

| Seedlings | Average weight of surviving seedlings (g) | | Infected seedlings weight as a percentage of control seedlings weight. |
|---|---|---|---|
| | Control (No. *R. solani*) | $4.0 \times 10^8$ *R. solani* propagules/tray | |
| 35SGUS | 0.089 | 0.047 | 53 |
| GOS-9 | 0.081 | 0.082 | 101 |
| GOS-13 | 0.082 | 0.090 | 110 |
| GOS-24 | 0.110 | 0.103 | 94 |
| GOT-9 | 0.086 | 0.094 | 109 |
| GOT-10 | 0.120 | 0.110 | 92 |
| GOT-21 | 0.085 | 0.068 | 80 |

REFERENCES:

An, G. et aL (1985) *EMBO J.*, 4, 277–84.

Ayer, W. A., Racok, J. S. (1990). *Can. J. Chem.*, 68, 2095–2101.

Bogusz, D., Llewellyn, D., Craig, S., Dennis, E. S., Appleby, C. and Peacock, W. J. (1990). *Plant Cell*, 2, 633–641.

Boosalis, M. G. (1956). *Phytopathology*, 46, 473–478.

Bradford, M. (1976). *Anal. Biochem.*, 72, 248–254.

Burke, T. J., Callis, J. and Vierstra, R. D. (1988). *Mol. Gen. Genet*, 213, 435–443.

Chen, J., Varner, M. (1985). *EMBO J.*, 4, 2145–2155.

Conkling, M. et al., (1990). *Plant. Physiol.*, 93, 1203–1211.

Cousins, Y. L., Lyon, B. R. and Llewellyn, D. J., (1991). *Aust. J. Plant Physiol.*, 18, 481–494.

Dolferus, R., Jacobs, M., Peacock, W. J. and Dennis, E. S. (1994). *Plant Physiol.*, 105, 1075–1087.

Fiedurek, J., Rogalski, J., Ilczuk, Z., Leonowicz, A. (1986). *Enzyme Microb. Technol.*, 8, 734–736.

Fitt, G. (1989). *Ann. Rev. Entomol.*, 34, 17–52.

Fravel, E. R., Kim, K. K., Papavizas, G. C. (1987). *Phytopathology*, 77, 616–619.

Frederick, K. R. et al., (1990). *J. Biol. Chem.*, 265, 3793–3802.

Hammer, J. E., Timberlake, W. E. (1987). *Mol. Cell Biol.*, 7, 2352–2359.

Hewitt, E. J. (1966). Sand and water culture methods used in the study of plant nutrition. 2nd edition, 187–193.
Kelley, R. L., Reddy, C. A. (1986). *J. Bact.,* 166, 269–274.
Kim, K. K., Fravel, d. R., Papavizas, G. C. (1988). *Phytopathology,* 78, 488–492.
Kim, K. K., Fravel, D. R., Papavizas, G. C. (1990a). *Can. J. Microbiol.,* 36, 199–205.
Kim, K. K., Fravel, D. R., Papavizas, G. C. ($_{1990}$b). *Can. J. Microbiol.,* 36, 760–764.
Kirschman, J. and Cramer, J. (1988), *Gene,* 68, 163–165.
Kriechbaum, M. et al. (1989). *FEBS Letters,* 255, 63–66.
Lazo, G. R., Stein, P. A. and Ludwig, R. A. (1991). *Bio/Technology,* 9, 963–967.
Loose, M. et al., (1991), *Gene,* 99, 95–100.
Lyon, B. R., Llewellyn, D. J., Huppatz, J. C., Dennis, E. S. and Peacock, W. J. (1989). *Plant MoL Biol.,* 13, 533–540.
MacLaren, D. L., Huang, H. C., Rimmer, S. R. (1986). *Can. J Plant. Path.,* 8, 43–48.
Madi, L., Fahima, T., Henis, Y. (1989). *J. Cellular Bioch.* Supplement 13(A), 178.
Marios, J. J., Johnson, S. A., Dunn, M. T., Papavizas, G. C. (1982). *Plant Disease,* 66, 1166–1168.
Muller, D. (1928). *Biochem.,* 199, 136.
Murray, F. R., Latch, G. C. M., Scott, D. B. (1992). *Mol. Gen. Genet.,* 233, 1–9.
Nakamura, S., Fujiki, S. (1968). *J. Biochem.,* 63, 51–58.
Odell, J. et al. (1985). *Nature,* 313, 810–812.
Olson, P. D. and Varner, J. E. (1993). *The Plant Journal,* 4, 887–892.
Orr-Weaver, T. L., Szostak, J. W., Rothstein, R. J. (1981). *Proc. Natl. Acad. Sci. (USA).*78, 6354–6358.
Perlak, F., et al., *Bio/Technology,* 8, 939–943.
Powell, P. et al., (1986). *Science,* 232, 738–743.
Puhalla, J. E. (1979). *Phytopathology,* 69, 1186–1189.
Punt, P. J. et al., (1987). *Gene,* 56, 117–124.
Raeder, U. and Broder, P., (1985). *Lett. Appl. Microbiol.,* 1, 17–20.
Sambrook, J., et al., (1989). *Molecular Cloning: A Laboratory Manual.* 2nd Edit. Cold Spring Harbor, N.Y., Cold Spring Harbor Press.
Schopfer, P. (1994). *Plant Physiol.,* 104, 1269–1275.
Stewart, J. M. D. and Hsu, C. L. (1977). *Planta,* 137, 113–117.
Tabe, L. M., Wardley-Richardson, T., Ceriotti, A., Aryan, A., McNabb, W., Moore, A. and Higgins, T. J. (1995). *J. Animal Science* (in press).
Whiftington, H., et al., (1990). *Current Genetics,* 18, 531–536.
Witteveen, F. B., van de Vondervoot, P., Swart, K., Visser, J. (1990). *Appl. Microbiol. Biotechnol.,* 33, 683–686.
Yamamoto, Y. T., Taylor, C. G., Acedo, G. N., Cheng, C. L. and Conkling, M. A. (1991). *Plant Cell,* 3, 371–382.

---

We claim:

1. A genetic construct comprising a nucleic acid segment having a nucleotide sequence encoding the glucose oxidase enzyme of *Talaromyces flavus*, said nucleic acid segment being operably linked to a promoter which directs expression in a plant, plant cell or group of plant cells, further comprising a nucleic acid segment having a nucleotide sequence encoding a signal sequence which directs secretion of the functional glucose oxidase enzyme of *T. flavus* from plant cells.

2. The genetic construct according to claim 1, wherein said promoter directs expression in cotton.

3. The genetic construct according to claim 1, wherein said promoter is a root specific promoter.

4. The genetic construct according to claim 3, wherein the promoter is selected from the group consisting of the root-specific pTOBRB7 promoter and the inducible extensin carrot root promoter.

5. The genetic construct according to claim 1, wherein said nucleic acid segment is represented by SEQ. ID NO: 1, or a portion of SEQ. ID No: 1 encoding a functional glucose oxidase enzyme of *T. flavus*.

6. The genetic construct according to claim 1, further comprising a nucleic acid segment having a nucleotide sequence encoding a signal sequence which directs secretion of functional glucose oxidase enzyme of *T. flavus* from plant cells.

7. The genetic construct according to claim 1, wherein the signal sequence is the secretion signal. sequence of the carrot root extensin gene.

8. A vector comprising a genetic construct according to claim 1.

9. A host organism which is a plant, a plant cell or a group of plant cells, comprising a vector according to claim 8.

10. The host organism according to claim 9, which is a cotton plant or a cotton plant cell or a group of cotton plant cells.

11. A transgenic organism which is a plant, L plant cell or a group of plant cells, comprising and expressing the genetic construct of claim 1.

12. The transgenic organism according to claim 11, which is a cotton plant or a cotton plant cell or a group of cotton plant cells.

13. A method of reducing susceptibility or increasing resistance of a host organism which is a plant cell or a group of plant cells to pests or diseases, which comprises transforming the host organism with a genetic construct according to claim 1.

14. The method according to claim 13, wherein said host organism is a cotton plant or a cotton plant cell or group of cotton plant cells.

15. The genetic construct according to claim 5, further comprising a nucleic acid segment having a nucleotide sequence encoding a signal sequence which directs secretion of functional glucose oxidase enzyme of *T. flavus* from plant cells.

16. The genetic construct according to claim 15, wherein the signal sequence is the secretion signal sequence of the carrot root extensin gene.

17. A method of reducing susceptibility or increasing resistance of a host organism which is a plant cell or a group of plant cells to pests or diseases, which comprises transforming the host organism with a vector comprising the genetic construct according to claim 1.

18. The method according to claim 17, wherein said host organism is a cotton plant or a cotton plant cell or group of cotton plant cells.

19. The genetic construct according to claim 1, wherein said promoter is an inducible promoter.

20. The method of claim 13, wherein the pest is selected from the group consisting of Verticillium sp., Helicoverpa sp., Pythium sp., Rhyzoctonia sp., and Sclerotina sp.

21. A genetic construct comprising a nucleic acid Segment having a nucleotide sequence encoding the glucose oxidase enzyme of *Talaromyces flavus*, said nucleic acid segment being operably linked to a promoter which directs expression in ct plant, plant cell or group of plant cells, and said genetic construct further comprising a nucleic acid segment having a nucleotide sequence encoding a signal sequence which directs the expression of the glucose oxidase enzyme such that expression of the genetic construct produces functional glucose oxidase enzyme of *Talaromyces flatus* that is secreted from plant cells.

* * * * *